United States Patent
Kato et al.

(10) Patent No.: US 10,906,972 B2
(45) Date of Patent: Feb. 2, 2021

(54) CANCER CELL SPECIFIC ANTI-PODOCALYXIN ANTIBODY AND METHOD FOR PRODUCING SAME

(71) Applicants: Tohoku University, Miyagi (JP); ZENOAQ RESOURCE CO., LTD., Fukushima (JP)

(72) Inventors: Yukinari Kato, Miyagi (JP); Mika Kaneko, Miyagi (JP); Satoshi Ogasawara, Miyagi (JP)

(73) Assignees: Tohoku University, Miyagi (JP); ZENOAQ RESOURCE CO., LTD., Fukushima (JP)

( * ) Notice: Subject to any disclaimer, the term of this patent is extended or adjusted under 35 U.S.C. 154(b) by 530 days.

(21) Appl. No.: 15/549,923

(22) PCT Filed: Feb. 12, 2016

(86) PCT No.: PCT/JP2016/054081
§ 371 (c)(1),
(2) Date: Dec. 12, 2017

(87) PCT Pub. No.: WO2016/129660
PCT Pub. Date: Aug. 18, 2016

(65) Prior Publication Data
US 2018/0134786 A1  May 17, 2018

(30) Foreign Application Priority Data
Feb. 12, 2015  (JP) ................................. 2015-025704

(51) Int. Cl.
| | | |
|---|---|---|
| C07K 16/28 | (2006.01) | |
| C12N 5/10 | (2006.01) | |
| G01N 33/574 | (2006.01) | |
| C12N 15/09 | (2006.01) | |
| C07K 16/30 | (2006.01) | |
| A61P 35/00 | (2006.01) | |
| A61K 39/00 | (2006.01) | |
| C12N 15/02 | (2006.01) | |

(52) U.S. Cl.
CPC .............. *C07K 16/28* (2013.01); *A61P 35/00* (2018.01); *C07K 16/2896* (2013.01); *C07K 16/30* (2013.01); *C12N 5/10* (2013.01); *C12N 15/02* (2013.01); *C12N 15/09* (2013.01); *G01N 33/574* (2013.01); *G01N 33/57492* (2013.01); *A61K 2039/505* (2013.01); *C07K 2317/24* (2013.01); *C07K 2317/41* (2013.01); *C07K 2317/52* (2013.01); *C07K 2317/565* (2013.01); *C07K 2317/732* (2013.01); *G01N 2333/705* (2013.01)

(58) Field of Classification Search
None
See application file for complete search history.

(56) References Cited

U.S. PATENT DOCUMENTS

| | | | | |
|---|---|---|---|---|
| 7,611,705 | B2* | 11/2009 | Chang | C07K 16/244 |
| | | | | 424/130.1 |
| 9,315,580 | B2* | 4/2016 | Banchereau | A61K 39/0011 |
| 10,370,451 | B2* | 8/2019 | Miyake | A61K 39/3955 |
| 2006/0294607 | A1 | 12/2006 | Fitzhugh et al. | |

FOREIGN PATENT DOCUMENTS

| | | |
|---|---|---|
| EP | 2452950 A1 | 5/2012 |
| WO | 2014095508 A1 | 6/2014 |
| WO | 2015058301 A1 | 4/2015 |

OTHER PUBLICATIONS

Horvat et al. (The Journal of Cell Biology, 1986, 102:484-491) (Year: 1986).*
Kaprio et al. (BMC Cancer, 2014, 14:493, pp. 1-7) (Year: 2014).*
Almagro & Fransson, Frontiers in Bioscience 2008; 13:1619-33 (Year: 2008).*
De Genst et al., Developmental and Comparative Immunology, 2006, 30:187-98 (Year: 2006).*
Ward et al. (Nature, 1989, 341:544-546) (Year: 1989).*
Barthelemy et al. (Journal of Biological Chemistry, 2008, 283:3639-3654) (Year: 2008).*
Choi et al., 2011, Molecular BioSystems, 2011, 7:3327-334 (Year: 2011).*
Griffiths et al. (The EMBO Journal, 1993, 12:725-734) t (Year: 1993).*
Klimka et al., British Journal of Cancer, 2000, 83:252-260 (Year: 2000).*
Beiboer et al. (Journal of Molecular Biology, 2000, 296:833-849) (Year: 2000).*
Ito, et al, "Extracellular and transmembrane region of a podocalyxin-like protein 1 fragment identified from colon cancer cell lines", Jul. 15, 2007, pp. 1518-1524, vol. 31, No. 12, Publisher: Cell Biology International.
Riccioni et al, "Podocalyxin is expressed in normal and leukemic monocytes", Oct. 23, 2006, pp. 218-225, vol. 37, No. 3, Publisher: Blood Cells Mol Dis.

(Continued)

*Primary Examiner* — Peter J Reddig
(74) *Attorney, Agent, or Firm* — Suzannah K. Sundby, Esq.; Canady + Lortz LLP

(57) ABSTRACT

The present invention provides a method for producing an antibody against podocalyxin expressed specifically in cancer cells. The method includes a step of introducing a nucleic acid encoding all or a portion of podocalyxin into cells expressing a cancer cell-specific sugar chain structure to cause cancer cell-specific podocalyxin or a portion thereof to be expressed therein, a step of immunizing a non-human mammal with the cancer cell-specific podocalyxin or portion thereof to obtain antibodies, and a step of purifying the antibodies by primary screening using purified cancer cell-specific podocalyxin or a portion thereof.

23 Claims, 5 Drawing Sheets
Specification includes a Sequence Listing.

(56) References Cited

OTHER PUBLICATIONS

Rodriguez et al., "Production and characterization of murine monoclonal antibodies against human podocalyxin", Nov. 7, 2006, pp. 407-417, vol. 68, No. 5, Publisher: Tissue Antigens.
International Search Report received in PCT/JP2016/054081 dated Apr. 12, 2016.
Written Opinion received in PCT/JP2016/054081 dated Apr. 12, 2016.
Casey, et al., "Podocalyxin variants and risk of prostate cancer and tumor aggressiveness", Mar. 1, 2006, p. 735-41, vol. 15, No. 5, Publisher: Hum Mol Genet.
Cipollone, et al., "The anti-adhesive mucin podocalyxin may help initiate the transperitoneal metastasis of high grade serous ovarian carcinoma", Mar. 1, 2012, p. 239-52, vol. 29, No. 3, Publisher: Clin Exp Metastasis.
Dallas, et al., "Sialofucosylated podocalyxin is a functional E- and L-selectin ligand expressed by metastatic pancreatic cancer cells", Sep. 15, 2012, p. C616-24, vol. 303, No. 6, Publisher: Am J Physiol Cell Physiol.
Hayatsu, et al., "Podocalyxin expression in malignant astrocytic tumors", Sep. 19, 2008, p. 394-8, vol. 374, No. 2, Publisher: Biochem Biophys Res Commun.
Kerjaschki, et al., "Identification of a major sialoprotein in the glycocalyx of human visceral glomerular epithelial cells", Nov. 1, 1986, p. 1142-9, vol. 78, No. 5, Publisher: J Clin Invest.
Larsson, et al., "Overexpression of podocalyxin-like protein is an independent factor of poor prognosis in colorectal cancer", Aug. 23, 2011, p. 666-72, vol. 105, No. 5, Publisher: Br J Cancer.
Larsson, et al., "Validation of podocalyxin-like protein as a biomarker of poor prognosis in colorectal cancer", Jul. 3, 2012, p. 282, vol. 12, Publisher: BMC Cancer.
Ogasawara, et al., "Development of Cancer-Specific Antibody (CasMab) against Podoplanin, 87th Annual Meeting", Oct. 18, 2014, pp. 4T13a-14 (4P-031), Publisher: The Japanese Biochemical Society.

Schopperle, et al., "Human embryonal carcinoma tumor antigen, Gp200/GCTM-2, is podocalyxin", Jan. 10, 2003, pp. 285-290, vol. 300, No. 2, Publisher: Biochemical and Biophysical Research Communications.
Schopperle, et al., "The TRA-1-60 and TRA-1-81 human pluripotent stem cell markers are expressed on podocalyxin in embryonal carcinoma", Mar. 1, 2007, p. 723-30, vol. 25, No. 3, Publisher: Stem Cells.
Snyder, et al, "Podocalyxin enhances breast tumor growth and metastasis and is a target for monoclonal antibody therapy", Mar. 27, 2015, p. 46 vol. 17, No. 1, Publisher: Breast Cancer Res.
Somasiri, et al., "Overexpression of the anti-adhesin podocalyxin is an independent predictor of breast cancer progression", Aug. 1, 2004, p. 5068-73, vol. 64, No. 15, Publisher: Cancer Research.
Takeda, et al., "Loss of glomerular foot processes is associated with uncoupling of podocalyxin from the actin cytoskeleton", Jul. 1, 2001, pp. 289-301, vol. 108, No. 2, Publisher: J Clin Invest.
Tateno, et al., "Podocalyxin is a glycoprotein ligand of the human pluripotent stem cell-specific probe rBC2LCN", Apr. 1, 2013, p. 265-73, vol. 2, No. 4, Publisher: Stem Cells Transl Med.
Thomas, et al., "Podocalyxin-like protein is an E-/L-selectin ligand on colon carcinoma cells: comparative biochemical properties of selectin ligands in host and tumor cells", Mar. 1, 2009, p. C505-13, vol. 296, No. 3, Publisher: Am J Physiol Cell Physiol
Yasuda, et al., "Rab27 effector Slp2-a transports the apical signaling molecule podocalyxin to the apical surface of MDCK II cells and regulates claudin-2 expression", Aug. 15, 2012, p. 32293239, vol. 23, No. 16, Publisher: Mol Biol Cell.
Gregoire et al., "Distinct glycoforms of a tumor specific glycoprotein, gp200, in human testis and testicular tumors", Jul. 1995, pp. 275-277, vol. 154, No. 1, Publisher: J Urol.
Kato et al., "A cancer-specific monoclonal antibody recognizes the aberrantly glycosylated podoplanin", Aug. 1, 2014, p. 5924, vol. 2014, No. 4, Publisher Scientific Reports.

* cited by examiner

[Fig. 1]
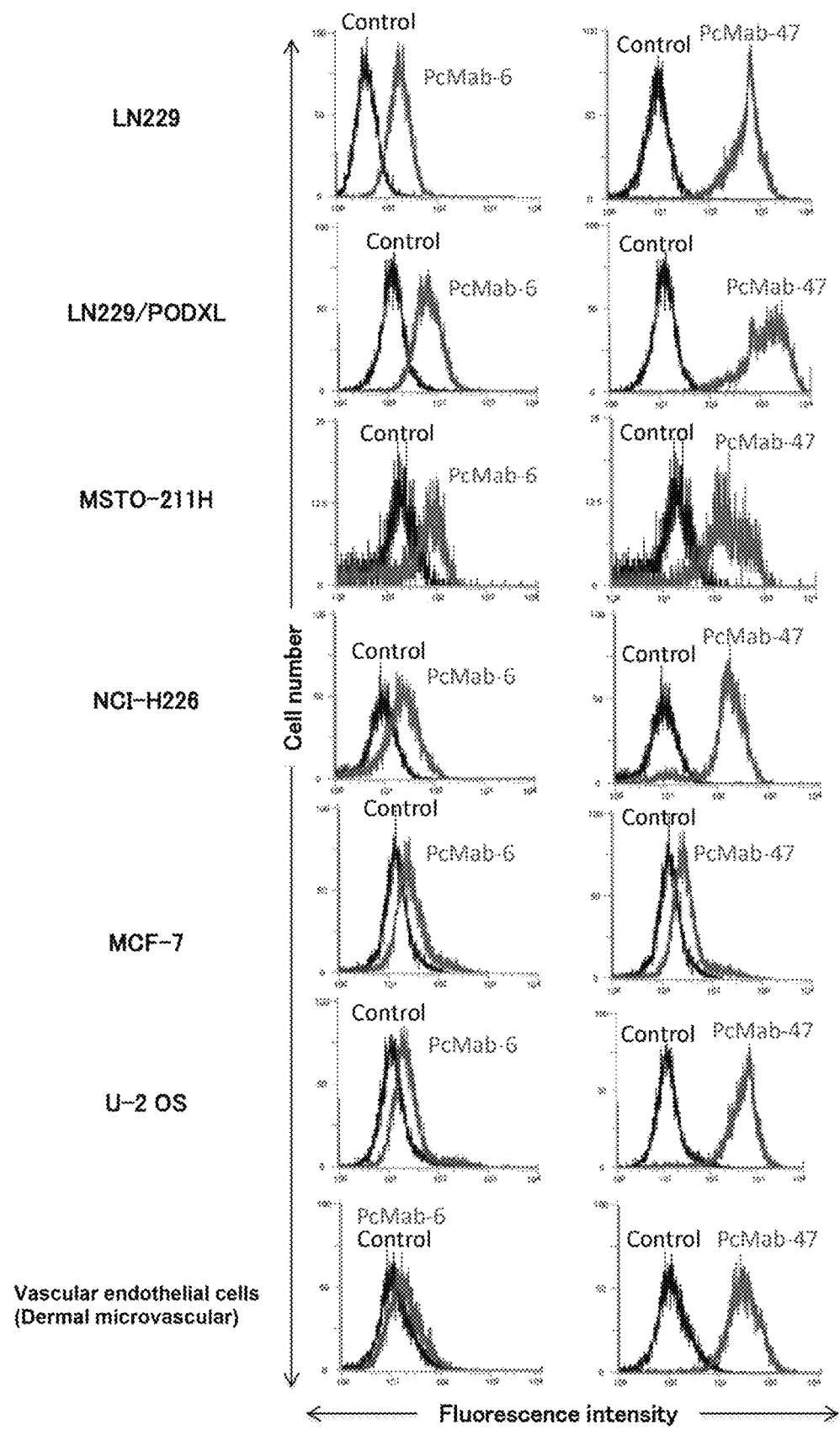

[Fig.2]
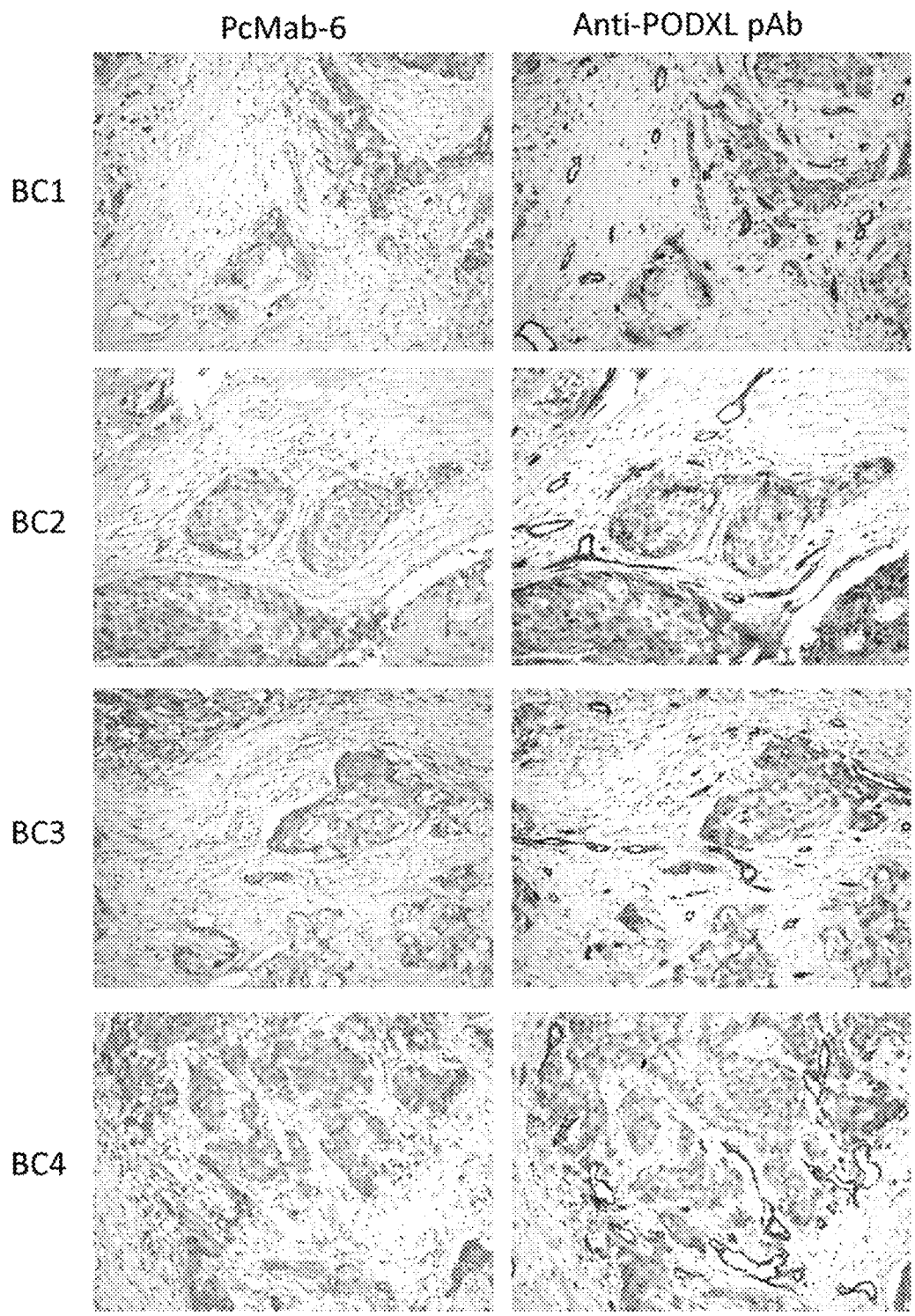

[Fig.3]
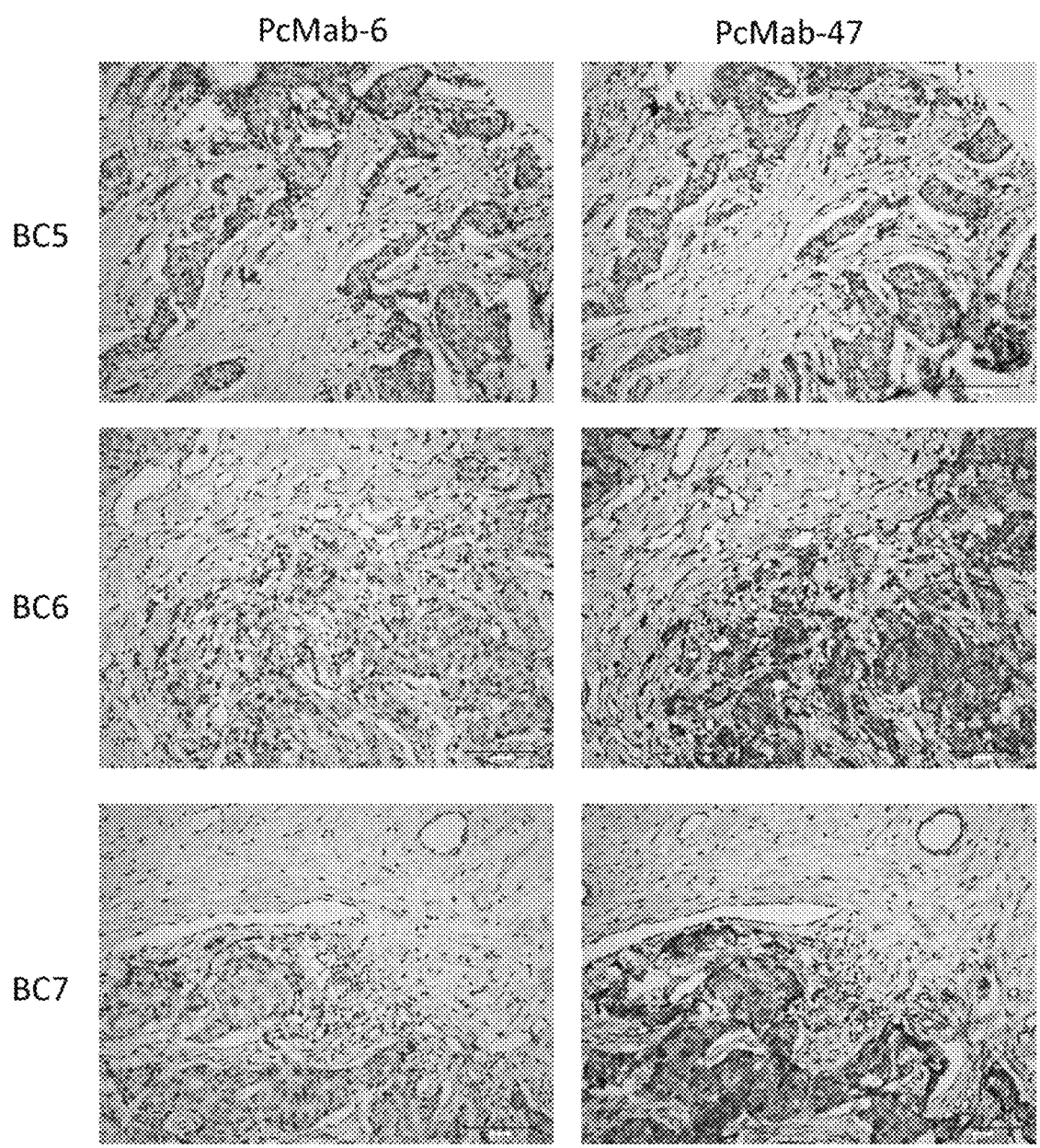

[Fig.4]
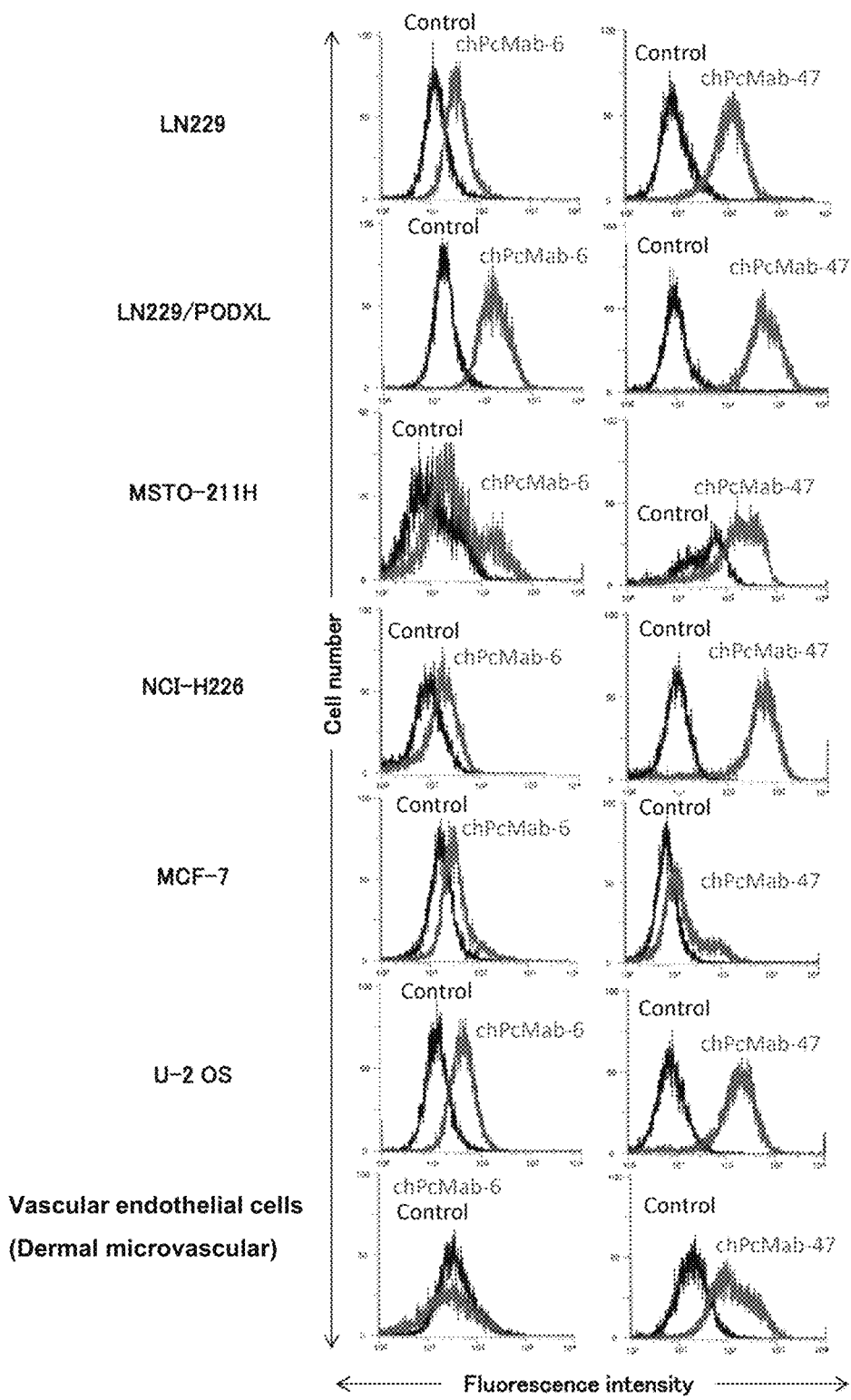

[Fig.5]
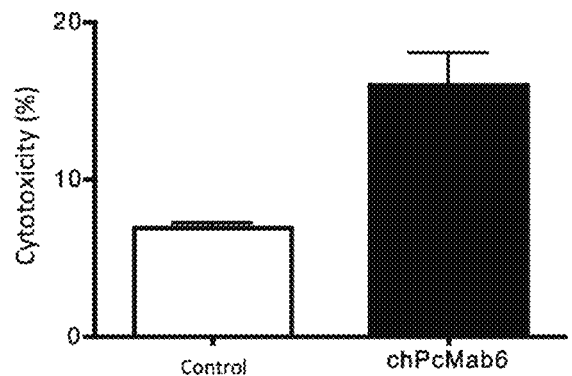
[Fig.6]
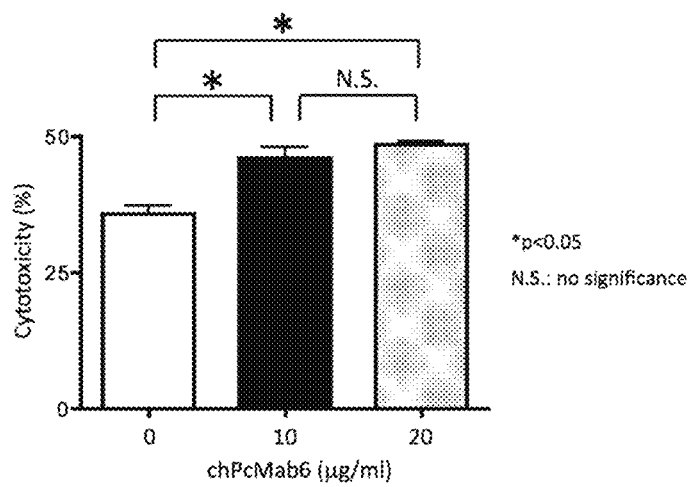
[Fig.7]
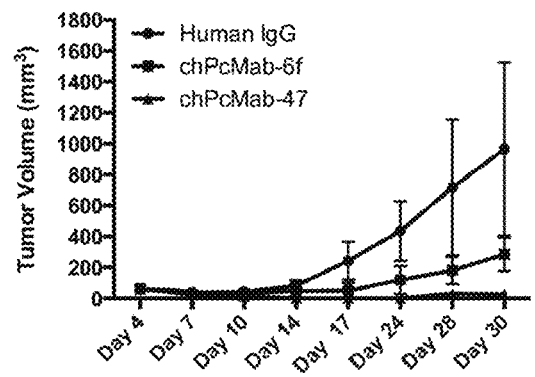

SEQUENCE LISTING

```
<160> NUMBER OF SEQ ID NOS: 41

<210> SEQ ID NO 1
<211> LENGTH: 558
<212> TYPE: PRT
<213> ORGANISM: Homo sapiens

<400> SEQUENCE: 1

Met Arg Cys Ala Leu Ala Leu Ser Ala Leu Leu Leu Leu Leu Ser Thr
1               5                   10                  15

Pro Pro Leu Leu Pro Ser Ser Pro Ser Pro Ser Pro Ser Pro Ser Gln
                20                  25                  30

Asn Ala Thr Gln Thr Thr Thr Asp Ser Ser Asn Lys Thr Ala Pro Thr
            35                  40                  45

Pro Ala Ser Ser Val Thr Ile Met Ala Thr Asp Thr Ala Gln Gln Ser
        50                  55                  60

Thr Val Pro Thr Ser Lys Ala Asn Glu Ile Leu Ala Ser Val Lys Ala
65                  70                  75                  80

Thr Thr Leu Gly Val Ser Ser Asp Ser Pro Gly Thr Thr Thr Leu Ala
                85                  90                  95

Gln Gln Val Ser Gly Pro Val Asn Thr Thr Val Ala Arg Gly Gly Gly
                100                 105                 110

Ser Gly Asn Pro Thr Thr Thr Ile Glu Ser Pro Lys Ser Thr Lys Ser
            115                 120                 125

Ala Asp Thr Thr Val Ala Thr Ser Thr Ala Thr Ala Lys Pro Asn
        130                 135                 140

Thr Thr Ser Ser Gln Asn Gly Ala Glu Asp Thr Thr Asn Ser Gly Gly
145                 150                 155                 160

Lys Ser Ser His Ser Val Thr Thr Asp Leu Thr Ser Thr Lys Ala Glu
                165                 170                 175
```

His Leu Thr Thr Pro His Pro Thr Ser Pro Leu Ser Pro Arg Gln Pro
                180                 185                 190

Thr Ser Thr His Pro Val Ala Thr Pro Thr Ser Ser Gly His Asp His
            195                 200                 205

Leu Met Lys Ile Ser Ser Ser Ser Thr Val Ala Ile Pro Gly Tyr
        210                 215                 220

Thr Phe Thr Ser Pro Gly Met Thr Thr Thr Leu Leu Glu Thr Val Phe
225                 230                 235                 240

His His Val Ser Gln Ala Gly Leu Glu Leu Leu Thr Ser Gly Asp Leu
                245                 250                 255

Pro Thr Leu Ala Ser Gln Ser Ala Gly Ile Thr Ala Ser Ser Val Ile
            260                 265                 270

Ser Gln Arg Thr Gln Gln Thr Ser Ser Gln Met Pro Ala Ser Ser Thr
        275                 280                 285

Ala Pro Ser Ser Gln Glu Thr Val Gln Pro Thr Ser Pro Ala Thr Ala
    290                 295                 300

Leu Arg Thr Pro Thr Leu Pro Glu Thr Met Ser Ser Ser Pro Thr Ala
305                 310                 315                 320

Ala Ser Thr Thr His Arg Tyr Pro Lys Thr Pro Ser Pro Thr Val Ala
                325                 330                 335

His Glu Ser Asn Trp Ala Lys Cys Glu Asp Leu Glu Thr Gln Thr Gln
            340                 345                 350

Ser Glu Lys Gln Leu Val Leu Asn Leu Thr Gly Asn Thr Leu Cys Ala
        355                 360                 365

Gly Gly Ala Ser Asp Glu Lys Leu Ile Ser Leu Ile Cys Arg Ala Val
    370                 375                 380

Lys Ala Thr Phe Asn Pro Ala Gln Asp Lys Cys Gly Ile Arg Leu Ala
385                 390                 395                 400

Ser Val Pro Gly Ser Gln Thr Val Val Lys Glu Ile Thr Ile His
                405                 410                 415

Thr Lys Leu Pro Ala Lys Asp Val Tyr Glu Arg Leu Lys Asp Lys Trp
            420                 425                 430

Asp Glu Leu Lys Glu Ala Gly Val Ser Asp Met Lys Leu Gly Asp Gln
        435                 440                 445

Gly Pro Pro Glu Glu Ala Glu Asp Arg Phe Ser Met Pro Leu Ile Ile
    450                 455                 460

Thr Ile Val Cys Met Ala Ser Phe Leu Leu Leu Val Ala Ala Leu Tyr
465                 470                 475                 480

Gly Cys Cys His Gln Arg Leu Ser Gln Arg Lys Asp Gln Gln Arg Leu
                485                 490                 495

Thr Glu Glu Leu Gln Thr Val Glu Asn Gly Tyr His Asp Asn Pro Thr
            500                 505                 510

Leu Glu Val Met Glu Thr Ser Ser Glu Met Gln Glu Lys Lys Val Val
        515                 520                 525

Ser Leu Asn Gly Glu Leu Gly Asp Ser Trp Ile Val Pro Leu Asp Asn
    530                 535                 540

Leu Thr Lys Asp Asp Leu Asp Glu Glu Asp Thr His Leu
545                 550                 555

<210> SEQ ID NO 2
<211> LENGTH: 10
<212> TYPE: PRT
<213> ORGANISM: Artificial
<220> FEATURE:

```
<223> OTHER INFORMATION: PcMab-6 heavy chain CDR1.

<400> SEQUENCE: 2

Gly Phe Asn Phe Asn Thr Asn Ala Met Asn
1               5                   10

<210> SEQ ID NO 3
<211> LENGTH: 19
<212> TYPE: PRT
<213> ORGANISM: Artificial
<220> FEATURE:
<223> OTHER INFORMATION: PcMab-6 heavy chain CDR2.

<400> SEQUENCE: 3

Leu Ile Arg Ser Lys Ser Asn Asn Tyr Ala Thr Tyr Tyr Ala Asp Ser
1               5                   10                  15

Val Lys Asp

<210> SEQ ID NO 4
<211> LENGTH: 5
<212> TYPE: PRT
<213> ORGANISM: Artificial
<220> FEATURE:
<223> OTHER INFORMATION: PcMab-6 heavy chain CDR3.

<400> SEQUENCE: 4

Gly Tyr Gly Ser Tyr
1               5

<210> SEQ ID NO 5
<211> LENGTH: 11
<212> TYPE: PRT
<213> ORGANISM: Artificial
<220> FEATURE:
<223> OTHER INFORMATION: PcMab-6 light chain CDR1.

<400> SEQUENCE: 5

Lys Ala Ser Gln Ser Val Asn Asn Asp Val Ala
1               5                   10

<210> SEQ ID NO 6
<211> LENGTH: 7
<212> TYPE: PRT
<213> ORGANISM: Artificial
<220> FEATURE:
<223> OTHER INFORMATION: PcMab-6 light chain CDR2.

<400> SEQUENCE: 6

Phe Ala Ser Asn Arg Tyr Thr
1               5

<210> SEQ ID NO 7
<211> LENGTH: 9
<212> TYPE: PRT
<213> ORGANISM: Artificial
<220> FEATURE:
<223> OTHER INFORMATION: PcMab-6 light chain CDR3.

<400> SEQUENCE: 7

Gln Leu Asp Tyr Asn Ser Thr Trp Thr
1               5

<210> SEQ ID NO 8
<211> LENGTH: 234
<212> TYPE: PRT
<213> ORGANISM: Artificial
```

<220> FEATURE:
<223> OTHER INFORMATION: PcMab-6 light chain CDR1.

<400> SEQUENCE: 8

Met Lys Ser Gln Thr Gln Val Phe Val Phe Leu Leu Leu Cys Val Ser
1               5                   10                  15

Gly Ala His Gly Ser Ile Val Met Thr Gln Thr Pro Lys Phe Leu Leu
            20                  25                  30

Val Ser Ala Gly Asp Arg Val Thr Ile Thr Cys Lys Ala Ser Gln Ser
        35                  40                  45

Val Asn Asn Asp Val Ala Trp Tyr Gln Gln Lys Pro Gly Gln Ser Pro
    50                  55                  60

Lys Leu Leu Ile Phe Phe Ala Ser Asn Arg Tyr Thr Gly Val Pro Asp
65                  70                  75                  80

Arg Phe Thr Gly Ser Gly Tyr Gly Thr Asp Phe Thr Phe Thr Ile Ser
                85                  90                  95

Asn Val Gln Ala Glu Asp Leu Ala Val Tyr Phe Cys Gln Leu Asp Tyr
            100                 105                 110

Asn Ser Thr Trp Thr Phe Gly Gly Gly Thr Lys Leu Glu Ile Lys Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
    210                 215                 220

Ile Val Lys Ser Phe Asn Arg Asn Glu Cys
225                 230

<210> SEQ ID NO 9
<211> LENGTH: 705
<212> TYPE: DNA
<213> ORGANISM: Artificial
<220> FEATURE:
<223> OTHER INFORMATION: PcMab-6 light chain.

<400> SEQUENCE: 9
atgaagtcac agacccaggt cttcgtattt ctactgctct gtgtgtctgg tgctcatggg    60
agtattgtga tgacccagac tcccaaattc ctgcttgtat cagcaggaga cagggttacc   120
ataacctgca aggccagtca gagtgtgaat aatgatgtag cttggtacca acagaagcca   180
gggcagtctc ctaaactgct gatattcttt gcatccaatc gctacactgg agtccctgat   240
cgcttcactg gcagtggata tgggacggat ttcacttca ccatcagcaa tgtacaggct   300
gaagacctgg cagtttattt ctgtcagctg gattataact ctacgtggac gttcggtgga   360
ggcaccaagc tggaaatcaa acgggctgat gctgcaccaa ctgtatccat cttcccacca   420
tccagtgagc agttaacatc tggaggtgcc tcagtcgtgt gcttcttgaa caacttctac   480
cccaaagaca tcaatgtcaa gtggaagatt gatggcagtg aacgacaaaa tggcgtcctg   540
aacagttgga ctgatcagga cagcaaagac agcacctaca gcatgagcag caccctcacg   600

```
ttgaccaagg acgagtatga acgacataac agctatacct gtgaggccac tcacaagaca    660
tcaacttcac ccattgtcaa gagcttcaac aggaatgagt gttag                    705
```

<210> SEQ ID NO 10
<211> LENGTH: 459
<212> TYPE: PRT
<213> ORGANISM: Artificial
<220> FEATURE:
<223> OTHER INFORMATION: PcMab-6 heavy chain.

<400> SEQUENCE: 10

```
Met Leu Leu Gly Leu Lys Trp Val Phe Phe Val Val Phe Tyr Gln Gly
 1               5                  10                  15

Val His Cys Glu Val Gln Leu Val Glu Thr Gly Gly Gly Leu Val Gln
            20                  25                  30

Pro Lys Gly Ser Leu Lys Leu Ser Cys Ala Ala Ser Gly Phe Asn Phe
        35                  40                  45

Asn Thr Asn Ala Met Asn Trp Val Arg Gln Ala Pro Gly Lys Gly Leu
    50                  55                  60

Glu Trp Val Ala Leu Ile Arg Ser Lys Ser Asn Asn Tyr Ala Thr Tyr
65                  70                  75                  80

Tyr Ala Asp Ser Val Lys Asp Arg Phe Thr Ile Ser Arg Asp Asp Glu
                85                  90                  95

Gln Ser Met Leu His Leu Gln Met Asn Asn Leu Lys Thr Glu Asp Thr
            100                 105                 110

Ala Ile Tyr Phe Cys Val Lys Gly Tyr Gly Ser Tyr Trp Gly Gln Gly
        115                 120                 125

Thr Thr Leu Thr Val Ser Ser Ala Lys Thr Thr Pro Pro Ser Val Tyr
    130                 135                 140

Pro Leu Ala Pro Gly Ser Ala Ala Gln Thr Asn Ser Met Val Thr Leu
145                 150                 155                 160

Gly Cys Leu Val Lys Gly Tyr Phe Pro Glu Pro Val Thr Val Thr Trp
                165                 170                 175

Asn Ser Gly Ser Leu Ser Ser Gly Val His Thr Phe Pro Ala Val Leu
            180                 185                 190

Gln Ser Asp Leu Tyr Thr Leu Ser Ser Ser Val Thr Val Pro Ser Ser
        195                 200                 205

Thr Trp Pro Ser Glu Thr Val Thr Cys Asn Val Ala His Pro Ala Ser
    210                 215                 220

Ser Thr Lys Val Asp Lys Lys Ile Val Pro Arg Asp Cys Gly Cys Lys
225                 230                 235                 240

Pro Cys Ile Cys Thr Val Pro Glu Val Ser Ser Val Phe Ile Phe Pro
                245                 250                 255

Pro Lys Pro Lys Asp Val Leu Thr Ile Thr Leu Thr Pro Lys Val Thr
            260                 265                 270

Cys Val Val Val Asp Ile Ser Lys Asp Asp Pro Glu Val Gln Phe Ser
        275                 280                 285

Trp Phe Val Asp Asp Val Glu Val His Thr Ala Gln Thr Gln Pro Arg
    290                 295                 300

Glu Glu Gln Phe Asn Ser Thr Phe Arg Ser Val Ser Glu Leu Pro Ile
305                 310                 315                 320

Met His Gln Asp Trp Leu Asn Gly Lys Glu Phe Lys Cys Arg Val Asn
                325                 330                 335

Ser Ala Ala Phe Pro Ala Pro Ile Glu Lys Thr Ile Ser Lys Thr Lys
```

```
            340                 345                 350
Gly Arg Pro Lys Ala Pro Gln Val Tyr Thr Ile Pro Pro Lys Glu
            355                 360                 365

Gln Met Ala Lys Asp Lys Val Ser Leu Thr Cys Met Ile Thr Asp Phe
        370                 375                 380

Phe Pro Glu Asp Ile Thr Val Glu Trp Gln Trp Asn Gly Gln Pro Ala
385                 390                 395                 400

Glu Asn Tyr Lys Asn Thr Gln Pro Ile Met Asp Thr Asp Gly Ser Tyr
                405                 410                 415

Phe Val Tyr Ser Lys Leu Asn Val Gln Lys Ser Asn Trp Glu Ala Gly
            420                 425                 430

Asn Thr Phe Thr Cys Ser Val Leu His Glu Gly Leu His Asn His His
        435                 440                 445

Thr Glu Lys Ser Leu Ser His Ser Pro Gly Lys
        450                 455
```

<210> SEQ ID NO 11
<211> LENGTH: 1380
<212> TYPE: DNA
<213> ORGANISM: Artificial
<220> FEATURE:
<223> OTHER INFORMATION: PcMab-6 heavy chain.

<400> SEQUENCE: 11

```
atgctgttgg ggctgaagtg ggtttctttt gttgttttt atcaaggtgt acattgtgag     60
gtgcagcttg ttgagactgg tgaggattg tgcagccta aagggtcatt gaaactctca    120
tgtgcagcct ctggattcaa cttcaatacc aatgccatga ctgggtccg ccaggctcca    180
ggaaagggtt tggaatgggt tgctctcata agaagtaaaa gtaataatta tgcaacatat    240
tatgccgatt cagtgaaaga caggttcacc atttccagag atgatgaaca aagcatgctc    300
catctgcaaa tgaacaactt gaaaactgag gacacagcca tttatttctg tgtgaagggc    360
tacggtagtt actggggcca aggcaccact ctcacagtct cctcagccaa aacgacaccc    420
ccatctgtct atccactggc ccctggatct gctgcccaaa ctaactccat ggtgaccctg    480
ggatgcctgg tcaagggcta tttccctgag ccagtgacag tgacctggaa ctctggatcc    540
ctgtccagcg gtgtgcacac cttcccagct gtcctgcagt ctgacctcta cactctgagc    600
agctcagtga ctgtccctc cagcacctgg cccagcgaga ccgtcacctg caacgttgcc    660
cacccggcca gcagcaccaa ggtggacaag aaaattgtgc cagggattg tggttgtaag    720
ccttgcatat gtacagtccc agaagtatca tctgtcttca tcttcccccc aaagcccaag    780
gatgtgctca ccattactct gactcctaag gtcacgtgtg ttgtggtaga catcagcaag    840
gatgatcccg aggtccagtt cagctggttt gtagatgatg tggaggtgca cacagctcag    900
acgcaacccc gggaggagca gttcaacagc actttccgct cagtcagtga acttcccatc    960
atgcaccagg actggctcaa tggcaaggag ttcaaatgca gggtcaacag tgcagctttc   1020
cctgccccca tcgagaaaac catctccaaa accaaaggca gaccgaaggc tccacaggtg   1080
tacaccattc cacctcccaa ggagcagatg gccaaggata agtcagtct gacctgcatg   1140
ataacagact tcttccctga agacattact gtggagtggc agtggaatgg cagccagcg   1200
gagaactaca agaacactca gcccatcatg gacacagatg gctcttactt cgtctacagc   1260
aagctcaatg tgcagaagag caactgggag gcaggaaata ctttcacctg ctctgtgtta   1320
catgagggcc tgcacaacca ccatactgag aagagcctct cccactctcc tggtaaatga   1380
```

```
<210> SEQ ID NO 12
<211> LENGTH: 30
<212> TYPE: DNA
<213> ORGANISM: Artificial
<220> FEATURE:
<223> OTHER INFORMATION: Primer HindIII-PcMab6HF1atg.

<400> SEQUENCE: 12
gctaagctta acatgctgtt ggggctgaag                                30

<210> SEQ ID NO 13
<211> LENGTH: 30
<212> TYPE: DNA
<213> ORGANISM: Artificial
<220> FEATURE:
<223> OTHER INFORMATION: Primer mIgG1terNotI.

<400> SEQUENCE: 13
ggcggccgct catttaccag gagagtggga                                30

<210> SEQ ID NO 14
<211> LENGTH: 34
<212> TYPE: DNA
<213> ORGANISM: Artificial
<220> FEATURE:
<223> OTHER INFORMATION: Primer InF.HindIII-Pc47H.

<400> SEQUENCE: 14
cggtatcgat aagcttaaca tggaaaggca ctgg                           34

<210> SEQ ID NO 15
<211> LENGTH: 34
<212> TYPE: DNA
<213> ORGANISM: Artificial
<220> FEATURE:
<223> OTHER INFORMATION: Primer InF.Pc47HterNotI.

<400> SEQUENCE: 15
tctagagtcg cggccgctca tttaccagga gagt                           34

<210> SEQ ID NO 16
<211> LENGTH: 30
<212> TYPE: DNA
<213> ORGANISM: Artificial
<220> FEATURE:
<223> OTHER INFORMATION: Primer HindIII-PcMab6L.F1atg.

<400> SEQUENCE: 16
gcgaagctta agatgaagtc acagacccag                                30

<210> SEQ ID NO 17
<211> LENGTH: 30
<212> TYPE: DNA
<213> ORGANISM: Artificial
<220> FEATURE:
<223> OTHER INFORMATION: Primer mIgCKterNotI.

<400> SEQUENCE: 17
ggcggccgcc taacactcat tcctgttgaa                                30

<210> SEQ ID NO 18
<211> LENGTH: 36
<212> TYPE: DNA
<213> ORGANISM: Artificial
<220> FEATURE:
<223> OTHER INFORMATION: Primer InF.HindIII-Pc47L.
```

<400> SEQUENCE: 18
cggtatcgat aagcttaaaa tggattttca ggtgca                                      36

<210> SEQ ID NO 19
<211> LENGTH: 34
<212> TYPE: DNA
<213> ORGANISM: Artificial
<220> FEATURE:
<223> OTHER INFORMATION: Primer InF.mIgCKterNotI.

<400> SEQUENCE: 19
tctagagtcg cggccgccta acactcattc ctgt                                        34

<210> SEQ ID NO 20
<211> LENGTH: 237
<212> TYPE: PRT
<213> ORGANISM: Artificial
<220> FEATURE:
<223> OTHER INFORMATION: PcMab-47 light chain.

<400> SEQUENCE: 20

Met Asp Phe Gln Val Gln Ile Phe Ser Phe Leu Leu Ile Ser Ala Ser
1               5                   10                  15

Val Ile Met Ser Arg Gly Gln Ile Val Leu Thr Gln Ser Pro Ala Ile
            20                  25                  30

Met Ser Ala Ser Leu Gly Glu Arg Val Thr Met Tyr Cys Thr Ala Ser
        35                  40                  45

Ser Ser Val Ser Ser Ser Tyr Leu His Trp Tyr Gln Gln Lys Pro Gly
    50                  55                  60

Ser Ser Pro Lys Leu Trp Ile Tyr Gly Thr Ser Asn Leu Ala Ser Gly
65                  70                  75                  80

Val Pro Ala Arg Phe Ser Gly Ser Gly Ser Gly Thr Ser Tyr Ser Leu
                85                  90                  95

Thr Ile Ser Ser Met Glu Ala Glu Asp Ala Ala Thr Tyr Tyr Cys His
            100                 105                 110

Gln Tyr His Arg Pro Pro Leu Thr Phe Gly Ala Gly Thr Lys Leu Glu
        115                 120                 125

Leu Lys Arg Ala Asp Ala Ala Pro Thr Val Ser Ile Phe Pro Pro Ser
    130                 135                 140

Ser Glu Gln Leu Thr Ser Gly Gly Ala Ser Val Val Cys Phe Leu Asn
145                 150                 155                 160

Asn Phe Tyr Pro Lys Asp Ile Asn Val Lys Trp Lys Ile Asp Gly Ser
                165                 170                 175

Glu Arg Gln Asn Gly Val Leu Asn Ser Trp Thr Asp Gln Asp Ser Lys
            180                 185                 190

Asp Ser Thr Tyr Ser Met Ser Ser Thr Leu Thr Leu Thr Lys Asp Glu
        195                 200                 205

Tyr Glu Arg His Asn Ser Tyr Thr Cys Glu Ala Thr His Lys Thr Ser
    210                 215                 220

Thr Ser Pro Ile Val Lys Ser Phe Asn Arg Asn Glu Cys
225                 230                 235

<210> SEQ ID NO 21
<211> LENGTH: 714
<212> TYPE: DNA
<213> ORGANISM: Artificial
<220> FEATURE:
<223> OTHER INFORMATION: PcMab-47 light chain.

<400> SEQUENCE: 21

```
atggattttc aggtgcagat tttcagcttc ctgctaatca gtgcctcagt cataatgtcc      60
agaggacaaa ttgttctcac ccagtctcca gcaatcatgt ctgcatctct aggggaacgg     120
gtcaccatgt actgcactgc cagctcaagt gtaagttcca gttacttgca ctggtaccag     180
cagaagccag atcctcccc caaactctgg atttatggca catccaacct ggcttctgga     240
gtcccagctc gcttcagtgg cagtgggtct gggacctctt actctctcac aatcagcagc     300
atggaggctg aagatgctgc cacttattac tgccaccaat atcatcgtcc cccgctcacg     360
ttcggtgctg ggaccaagct ggagctgaaa cgggctgatg ctgccaccaac tgtatccatc     420
ttcccaccat ccagtgagca gttaacatct ggaggtgcct cagtcgtgtg cttcttgaac     480
aacttctacc ccaaagacat caatgtcaag tggaagattg atggcagtga acgacaaaat     540
ggcgtcctga acagttggac tgatcaggac agcaaagaca gcacctacag catgagcagc     600
accctcacgt tgaccaagga cgagtatgaa cgacataaca gctatacctg tgaggccact     660
cacaagacat caacttcacc cattgtcaag agcttcaaca ggaatgagtg ttag           714
```

<210> SEQ ID NO 22
<211> LENGTH: 458
<212> TYPE: PRT
<213> ORGANISM: Artificial
<220> FEATURE:
<223> OTHER INFORMATION: PcMab-47 heavy chain.

<400> SEQUENCE: 22

```
Met Glu Arg His Trp Ile Phe Leu Phe Leu Leu Ser Val Thr Ala Gly
1               5                   10                  15

Val His Ser Gln Val Gln Leu Gln Gln Ser Ala Ala Glu Leu Ala Arg
            20                  25                  30

Pro Gly Ala Ser Val Lys Met Ser Cys Lys Ala Ser Gly Tyr Thr Phe
        35                  40                  45

Thr Asn Tyr Thr Ile His Trp Val Lys Gln Arg Pro Gly Gln Gly Leu
    50                  55                  60

Glu Trp Ile Gly Phe Ile Asn Pro Thr Ser Gly Tyr Ser Asp Phe Asn
65                  70                  75                  80

Gln Lys Phe Lys Ala Lys Thr Thr Leu Thr Ala Asp Lys Ser Ser Ser
                85                  90                  95

Thr Ala His Met Gln Leu Thr Ser Leu Thr Ser Glu Asp Ser Ala Val
            100                 105                 110

Tyr Tyr Cys Ala Arg Leu Phe Ala Pro Ala Tyr Trp Gly Gln Gly Thr
        115                 120                 125

Leu Val Thr Val Ser Ala Ala Lys Thr Thr Pro Pro Ser Val Tyr Pro
    130                 135                 140

Leu Ala Pro Gly Ser Ala Ala Gln Thr Asn Ser Met Val Thr Leu Gly
145                 150                 155                 160

Cys Leu Val Lys Gly Tyr Phe Pro Glu Pro Val Thr Val Thr Trp Asn
                165                 170                 175

Ser Gly Ser Leu Ser Ser Gly Val His Thr Phe Pro Ala Val Leu Gln
            180                 185                 190

Ser Asp Leu Tyr Thr Leu Ser Ser Ser Val Thr Val Pro Ser Ser Thr
        195                 200                 205

Trp Pro Ser Glu Thr Val Thr Cys Asn Val Ala His Pro Ala Ser Ser
    210                 215                 220
```

```
Thr Lys Val Asp Lys Lys Ile Val Pro Arg Asp Cys Gly Cys Lys Pro
225                 230                 235                 240

Cys Ile Cys Thr Val Pro Glu Val Ser Ser Val Phe Ile Phe Pro Pro
            245                 250                 255

Lys Pro Lys Asp Val Leu Thr Ile Thr Leu Thr Pro Lys Val Thr Cys
        260                 265                 270

Val Val Val Asp Ile Ser Lys Asp Asp Pro Glu Val Gln Phe Ser Trp
    275                 280                 285

Phe Val Asp Asp Val Glu Val His Thr Ala Gln Thr Gln Pro Arg Glu
290                 295                 300

Glu Gln Phe Asn Ser Thr Phe Arg Ser Val Ser Glu Leu Pro Ile Met
305                 310                 315                 320

His Gln Asp Trp Leu Asn Gly Lys Glu Phe Lys Cys Arg Val Asn Ser
            325                 330                 335

Ala Ala Phe Pro Ala Pro Ile Glu Lys Thr Ile Ser Lys Thr Lys Gly
        340                 345                 350

Arg Pro Lys Ala Pro Gln Val Tyr Thr Ile Pro Pro Lys Glu Gln
    355                 360                 365

Met Ala Lys Asp Lys Val Ser Leu Thr Cys Met Ile Thr Asp Phe Phe
370                 375                 380

Pro Glu Asp Ile Thr Val Glu Trp Gln Trp Asn Gly Gln Pro Ala Glu
385                 390                 395                 400

Asn Tyr Lys Asn Thr Gln Pro Ile Met Asp Thr Asp Gly Ser Tyr Phe
            405                 410                 415

Val Tyr Ser Lys Leu Asn Val Gln Lys Ser Asn Trp Glu Ala Gly Asn
        420                 425                 430

Thr Phe Thr Cys Ser Val Leu His Glu Gly Leu His Asn His His Thr
    435                 440                 445

Glu Lys Ser Leu Ser His Ser Pro Gly Lys
450                 455
```

<210> SEQ ID NO 23
<211> LENGTH: 1377
<212> TYPE: DNA
<213> ORGANISM: Artificial
<220> FEATURE:
<223> OTHER INFORMATION: PcMab-47 heavy chain.

<400> SEQUENCE: 23

```
atggaaaggc actggatctt tctcttcctg ttgtcagtaa ctgcaggtgt ccactcccag    60
gtccagctgc agcagtctgc agctgaactg gcaagacctg ggcctcagt gaagatgtcc   120
tgcaaggctt ctggctacac ctttactaac tacacgatac actgggtaaa acagaggcct   180
ggacagggtc tggaatggat tggattcatt aatcctacca gtggatattc tgacttcaat   240
cagaagttca aggccaagac acattgact gcggacaaat cctccagcac agcccacatg   300
caactgacca gctgacatc tgaggactct gcggtctatt actgtgcaag actcttcgct   360
cctgcttact ggggccaagg gactctggtc actgtctctg cagccaaaac gacaccccca   420
tctgtctatc cactggcccc tggatctgct gcccaaacta actccatggt gaccctggga   480
tgcctggtca aggctatttt ccctgagcca gtgacagtga cctggaactc tggatccctg   540
tccagcggtg tgcacacctt cccagctgtc ctgcagtctg acctctacac tctgagcagc   600
tcagtgactg tcccctccag cacctggccc agcgagaccg tcacctgcaa cgttgcccac   660
ccggccagca gcaccaaggt ggacaagaaa attgtgccca gggattgtgg ttgtaagcct   720
```

```
tgcatatgta cagtcccaga agtatcatct gtcttcatct tcccccaaa gcccaaggat    780 gtgctcacca ttactctgac tcctaaggtc acgtgtgttg tggtagacat cagcaaggat    840
gatcccgagg tccagttcag ctggtttgta gatgatgtgg aggtgcacac agctcagacg    900
caaccccggg aggagcagtt caacagcact ttccgctcag tcagtgaact tcccatcatg    960
caccaggact ggctcaatgg caaggagttc aaatgcaggg tcaacagtgc agctttccct   1020
gcccccatcg agaaaaccat ctccaaaacc aaaggcagac cgaaggctcc acaggtgtac   1080
accattccac ctcccaagga gcagatggcc aaggataaag tcagtctgac ctgcatgata   1140
acagacttct tccctgaaga cattactgtg gagtggcagt ggaatgggca gccagcggag   1200
aactacaaga cactcagcc catcatggac acagatggct cttacttcgt ctacagcaag   1260
ctcaatgtgc agaagagcaa ctgggaggca ggaaatactt tcacctgctc tgtgttacat   1320
gagggcctgc acaaccacca tactgagaag agcctctccc actctcctgg taaatga      1377
```

<210> SEQ ID NO 24
<211> LENGTH: 10
<212> TYPE: PRT
<213> ORGANISM: Artificial
<220> FEATURE:
<223> OTHER INFORMATION: PcMab-47 heavy chain CDR1.

<400> SEQUENCE: 24

Gly Tyr Thr Phe Thr Asn Tyr Thr Ile His
1               5                   10

<210> SEQ ID NO 25
<211> LENGTH: 17
<212> TYPE: PRT
<213> ORGANISM: Artificial
<220> FEATURE:
<223> OTHER INFORMATION: PcMab-47 heavy chain CDR2.

<400> SEQUENCE: 25

Phe Ile Asn Pro Thr Ser Gly Tyr Ser Asp Phe Asn Gln Lys Phe Lys
1               5                   10                  15

Ala

<210> SEQ ID NO 26
<211> LENGTH: 6
<212> TYPE: PRT
<213> ORGANISM: Artificial
<220> FEATURE:
<223> OTHER INFORMATION: PcMab-47 heavy chain CDR3.

<400> SEQUENCE: 26

Leu Phe Ala Pro Ala Tyr
1               5

<210> SEQ ID NO 27
<211> LENGTH: 12
<212> TYPE: PRT
<213> ORGANISM: Artificial
<220> FEATURE:
<223> OTHER INFORMATION: PcMab-47 light chain CDR1.

<400> SEQUENCE: 27

Thr Ala Ser Ser Ser Val Ser Ser Ser Tyr Leu His
1               5                   10

<210> SEQ ID NO 28
<211> LENGTH: 7

```
<212> TYPE: PRT
<213> ORGANISM: Artificial
<220> FEATURE:
<223> OTHER INFORMATION: PcMab-47 light chain CDR2.

<400> SEQUENCE: 28

Gly Thr Ser Asn Leu Ala Ser
1               5

<210> SEQ ID NO 29
<211> LENGTH: 9
<212> TYPE: PRT
<213> ORGANISM: Artificial
<220> FEATURE:
<223> OTHER INFORMATION: PcMab-47 light chain CDR3.

<400> SEQUENCE: 29

His Gln Tyr His Arg Pro Pro Leu Thr
1               5

<210> SEQ ID NO 30
<211> LENGTH: 30
<212> TYPE: DNA
<213> ORGANISM: Artificial
<220> FEATURE:
<223> OTHER INFORMATION: Primer PcMab6VHR-BamHI.

<400> SEQUENCE: 30
gccggatcct gaggagactg tgagagtggt                                      30

<210> SEQ ID NO 31
<211> LENGTH: 33
<212> TYPE: DNA
<213> ORGANISM: Artificial
<220> FEATURE:
<223> OTHER INFORMATION: Primer InFr.PcMab47VHR-BamHI.

<400> SEQUENCE: 31
ggcccttggt ggatcctgca gagacagtga cca                                  33

<210> SEQ ID NO 32
<211> LENGTH: 30
<212> TYPE: DNA
<213> ORGANISM: Artificial
<220> FEATURE:
<223> OTHER INFORMATION: Primer PcMab6LVL-BamHI.

<400> SEQUENCE: 32
gccggatccc cgtttgattt ccagcttggt                                      30

<210> SEQ ID NO 33
<211> LENGTH: 33
<212> TYPE: DNA
<213> ORGANISM: Artificial
<220> FEATURE:
<223> OTHER INFORMATION: Primer InF.PcMab47LVL-SpeI.

<400> SEQUENCE: 33
cagccacagt actagtccgt ttcagctcca gct                                  33

<210> SEQ ID NO 34
<211> LENGTH: 465
<212> TYPE: PRT
<213> ORGANISM: Artificial
<220> FEATURE:
<223> OTHER INFORMATION: chPcMab-6 heavy chain.
```

<400> SEQUENCE: 34

```
Met Leu Leu Gly Leu Lys Trp Val Phe Phe Val Val Phe Tyr Gln Gly
1               5                   10                  15

Val His Cys Glu Val Gln Leu Val Glu Thr Gly Gly Gly Leu Val Gln
            20                  25                  30

Pro Lys Gly Ser Leu Lys Leu Ser Cys Ala Ala Ser Gly Phe Asn Phe
        35                  40                  45

Asn Thr Asn Ala Met Asn Trp Val Arg Gln Ala Pro Gly Lys Gly Leu
    50                  55                  60

Glu Trp Val Ala Leu Ile Arg Ser Lys Ser Asn Asn Tyr Ala Thr Tyr
65                  70                  75                  80

Tyr Ala Asp Ser Val Lys Asp Arg Phe Thr Ile Ser Arg Asp Asp Glu
                85                  90                  95

Gln Ser Met Leu His Leu Gln Met Asn Asn Leu Lys Thr Glu Asp Thr
            100                 105                 110

Ala Ile Tyr Phe Cys Val Lys Gly Tyr Gly Ser Tyr Trp Gly Gln Gly
        115                 120                 125

Thr Thr Leu Thr Val Ser Ser Gly Ser Thr Lys Gly Pro Ser Val Phe
130                 135                 140

Pro Leu Ala Pro Cys Ser Arg Ser Thr Ser Glu Ser Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Asn Phe Gly Thr Gln Thr Tyr Thr Cys Asn Val Asp His Lys Pro
    210                 215                 220

Ser Asn Thr Lys Val Asp Lys Thr Val Glu Pro Lys Ser Cys Asp Lys
225                 230                 235                 240

Thr His Thr Cys Pro Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Gln Phe Asn Trp Tyr Val Asp Gly Val Glu Val His Asn
    290                 295                 300

Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Ala Leu Pro Ala Pro Ile Glu Lys
            340                 345                 350

Thr Ile Ser Lys Ala Lys Gly Gln Pro Arg Glu Pro Gln Val Tyr Thr
        355                 360                 365

Leu Pro Pro Ser Arg Asp Glu Leu Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415
```

```
Asp Ser Asp Gly Ser Phe Phe Leu Tyr Ser Lys Leu Thr Val Asp Lys
                420                 425                 430

Ser Arg Trp Gln Gln Gly Asn Val Phe Ser Cys Ser Val Met His Glu
            435                 440                 445

Ala Leu His Asn His Tyr Thr Gln Lys Ser Leu Ser Leu Ser Pro Gly
        450                 455                 460

Lys
465

<210> SEQ ID NO 35
<211> LENGTH: 1398
<212> TYPE: DNA
<213> ORGANISM: Artificial
<220> FEATURE:
<223> OTHER INFORMATION: chPcMab-6 heavy chain.

<400> SEQUENCE: 35
atgctgttgg ggctgaagtg ggttttcttt gttgtttttt atcaaggtgt acattgtgag      60
gtgcagcttg ttgagactgg tggaggattg gtgcagccta agggtcatt gaaactctca     120
tgtgcagcct ctggattcaa cttcaatacc aatgccatga actgggtccg ccaggctcca    180
ggaaagggtt tggaatgggt tgctctcata agaagtaaaa gtaataatta tgcaacatat    240
tatgccgatt cagtgaaaga caggttcacc atttccagag atgatgaaca agcatgctc     300
catctgcaaa tgaacaactt gaaaactgag gacacagcca tttatttctg tgtgaagggc    360
tacggtagtt actggggcca aggcaccact ctcacagtct cctcaggatc caccaagggc    420
ccatcggtct tccccctggc gccctgctcc aggagcacct ccgagagcac agcggccctg    480
ggctgcctgg tcaaggacta cttccccgaa ccggtgacgg tgtcgtggaa ctcaggcgct    540
ctgaccagcg gcgtgcacac cttcccagct gtcctacagt cctcaggact ctactccctc    600
agcagcgtgg tgaccgtgcc ctccagcaac ttcggcaccc agacctacac ctgcaacgta    660
gatcacaagc ccagcaacac caaggtggac aagacagttg agcccaaatc ttgtgacaaa    720
actcacacat gcccaccgtg cccagcacct gaactcctgg ggggaccgtc agtcttcctc    780
ttccccccaa aacccaagga caccctcatg atctcccgga cccctgaggt cacgtgcgtg    840
gtggtggacg tgagccacga agaccccgag gtccagttca actggtacgt ggacggcgtg    900
gaggtgcata atgccaagac aaagccgcgg gaggagcagt acaacagcac gtaccgtgtg    960
gtcagcgtcc tcaccgtcct gcaccaggac tggctgaatg gcaaggagta caaatgcaag   1020
gtctccaaca aagccctccc agcccccatc gagaaaacca tctccaaagc caagggcag   1080
ccccgagaac cacaggtgta caccctgccc ccatcccggg atgagctgac caagaaccag   1140
gtcagcctga cctgcctggt caaaggcttc tatcccagcg acatcgccgt ggagtgggag   1200
agcaatgggc agccggagaa caactacaag accacgcctc ccgtgctgga ctccgacggc   1260
tccttcttcc tttacagcaa gctcaccgtg gacaagagca ggtggcagca ggggaacgtc   1320
ttctcatgct ccgtgatgca tgaggctctg cacaaccact acacgcagaa gagcctctcc   1380
ctgtctccgg gtaaatga                                                 1398

<210> SEQ ID NO 36
<211> LENGTH: 236
<212> TYPE: PRT
<213> ORGANISM: Artificial
<220> FEATURE:
<223> OTHER INFORMATION: chPcMab-6 light chain.
```

<400> SEQUENCE: 36

Met Lys Ser Gln Thr Gln Val Phe Val Phe Leu Leu Leu Cys Val Ser
1               5                   10                  15

Gly Ala His Gly Ser Ile Val Met Thr Gln Thr Pro Lys Phe Leu Leu
            20                  25                  30

Val Ser Ala Gly Asp Arg Val Thr Ile Thr Cys Lys Ala Ser Gln Ser
        35                  40                  45

Val Asn Asn Asp Val Ala Trp Tyr Gln Gln Lys Pro Gly Gln Ser Pro
    50                  55                  60

Lys Leu Leu Ile Phe Phe Ala Ser Asn Arg Tyr Thr Gly Val Pro Asp
65                  70                  75                  80

Arg Phe Thr Gly Ser Gly Tyr Gly Thr Asp Phe Thr Phe Thr Ile Ser
                85                  90                  95

Asn Val Gln Ala Glu Asp Leu Ala Val Tyr Phe Cys Leu Asp Tyr
            100                 105                 110

Asn Ser Thr Trp Thr Phe Gly Gly Gly Thr Lys Leu Glu Ile Lys Arg
            115                 120                 125

Gly Ser Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 37
<211> LENGTH: 711
<212> TYPE: DNA
<213> ORGANISM: Artificial
<220> FEATURE:
<223> OTHER INFORMATION: chPcMab-6 light chain.

<400> SEQUENCE: 37

```
atgaagtcac agacccaggt cttcgtattt ctactgctct gtgtgtctgg tgctcatggg      60
agtattgtga tgacccagac tcccaaattc ctgcttgtat cagcaggaga cagggttacc     120
ataacctgca aggccagtca gagtgtgaat aatgatgtag cttggtacca acagaagcca     180
gggcagtctc ctaaactgct gatattcttt gcatccaatc gctacactgg agtccctgat     240
cgcttcactg gcagtggata tgggacggat ttcactttca ccatcagcaa tgtacaggct     300
gaagacctgg cagtttattt ctgtcagctg gattataact ctacgtggac gttcggtgga     360
ggcaccaagc tggaaatcaa acggggatcc actgtggctg caccatctgt cttcatcttc     420
ccgccatctg atgagcagtt gaaatctgga actgcctctg ttgtgtgcct gctgaataac     480
ttctatccca gagaggccaa agtacagtgg aaggtggata acgccctcca atcgggtaac     540
tcccaggaga gtgtcacaga gcaggacagc aaggacagca cctacagcct cagcagcacc     600
ctgacgctga gcaaagcaga ctacgagaaa cacaaagtct acgcctgcga agtcacccat     660
```
cagggcctga gctcgcccgt cacaaagagc ttcaacaggg gagagtgtta g            711

<210> SEQ ID NO 38
<211> LENGTH: 464
<212> TYPE: PRT
<213> ORGANISM: Artificial
<220> FEATURE:
<223> OTHER INFORMATION: chPcMab-47 heavy chain.

<400> SEQUENCE: 38

```
Met Glu Arg His Trp Ile Phe Leu Phe Leu Leu Ser Val Thr Ala Gly
1               5                   10                  15

Val His Ser Gln Val Gln Leu Gln Gln Ser Ala Ala Glu Leu Ala Arg
            20                  25                  30

Pro Gly Ala Ser Val Lys Met Ser Cys Lys Ala Ser Gly Tyr Thr Phe
        35                  40                  45

Thr Asn Tyr Thr Ile His Trp Val Lys Gln Arg Pro Gly Gln Gly Leu
    50                  55                  60

Glu Trp Ile Gly Phe Ile Asn Pro Thr Ser Gly Tyr Ser Asp Phe Asn
65                  70                  75                  80

Gln Lys Phe Lys Ala Lys Thr Thr Leu Thr Ala Asp Lys Ser Ser Ser
                85                  90                  95

Thr Ala His Met Gln Leu Thr Ser Leu Thr Ser Glu Asp Ser Ala Val
            100                 105                 110

Tyr Tyr Cys Ala Arg Leu Phe Ala Pro Ala Tyr Trp Gly Gln Gly Thr
        115                 120                 125

Leu Val Thr Val Ser Ala Gly Ser Thr Lys Gly Pro Ser Val Phe Pro
130                 135                 140

Leu Ala Pro Cys Ser Arg Ser Thr Ser Glu Ser Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Asn Phe Gly Thr Gln Thr Tyr Thr Cys Asn Val Asp His Lys Pro Ser
    210                 215                 220

Asn Thr Lys Val Asp Lys Thr Val Glu Pro Lys Ser Cys Asp Lys Thr
225                 230                 235                 240

His Thr Cys Pro Pro Cys Pro Ala Pro Glu Leu Leu Gly Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser His Glu Asp Pro
        275                 280                 285

Glu Val Gln Phe Asn Trp Tyr Val Asp Gly Val Glu Val His Asn Ala
    290                 295                 300

Lys Thr Lys Pro Arg Glu Glu Gln Tyr Asn Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Ala Leu Pro Ala Pro Ile Glu Lys Thr
            340                 345                 350

Ile Ser Lys Ala Lys Gly Gln Pro Arg Glu Pro Gln Val Tyr Thr Leu
```

|     | 355 |     |     |     | 360 |     |     |     | 365 |     |     |
|-----|-----|-----|-----|-----|-----|-----|-----|-----|-----|-----|-----|

Pro Pro Ser Arg Asp Glu Leu Thr Lys Asn Gln Val Ser Leu Thr Cys
370                     375                     380

Leu Val Lys Gly Phe Tyr Pro Ser Asp Ile Ala Val Glu Trp Glu Ser
385                     390                     395                     400

Asn Gly Gln Pro Glu Asn Asn Tyr Lys Thr Thr Pro Pro Val Leu Asp
                405                     410                     415

Ser Asp Gly Ser Phe Phe Leu Tyr Ser Lys Leu Thr Val Asp Lys Ser
            420                     425                     430

Arg Trp Gln Gln Gly Asn Val Phe Ser Cys Ser Val Met His Glu Ala
                435                     440                     445

Leu His Asn His Tyr Thr Gln Lys Ser Leu Ser Leu Ser Pro Gly Lys
450                     455                     460

<210> SEQ ID NO 39
<211> LENGTH: 1395
<212> TYPE: DNA
<213> ORGANISM: Artificial
<220> FEATURE:
<223> OTHER INFORMATION: chPcMab-47 heavy chain.

<400> SEQUENCE: 39

```
atggaaaggc actggatctt tctcttcctg ttgtcagtaa ctgcaggtgt ccactcccag      60
gtccagctgc agcagtctgc agctgaactg gcaagacctg gggcctcagt gaagatgtcc     120
tgcaaggctt ctggctacac ctttactaac tacacgatac actgggtaaa acagaggcct     180
ggacagggtc tggaatggat tggattcatt aatcctacca gtggatattc tgacttcaat     240
cagaagttca aggccaagac cacattgact gcggacaaat cctccagcac agcccacatg     300
caactgacca gcctgacatc tgaggactct gcggtctatt actgtgcaag actcttcgct     360
cctgcttact ggggccaagg gactctggtc actgtctctg caggatccac caagggccca     420
tcggtcttcc cctggcgcc tgctccagg agcacctccg agcacagc ggccctgggc          480
tgcctggtca aggactactt ccccgaaccg gtgacggtgt cgtggaactc aggcgctctg     540
accagcggcg tgcacacctt cccagctgtc ctacagtcct caggactcta ctccctcagc     600
agcgtggtga ccgtgccctc agcaacttc ggcacccaga cctacacctg caacgtagat      660
cacaagccca gcaacaccaa ggtggacaag acagttgagc ccaaatcttg tgacaaaact     720
cacacatgcc caccgtgccc agcacctgaa ctcctggggg gaccgtcagt cttcctcttc     780
cccccaaaac ccaaggacac cctcatgatc tcccggaccc ctgaggtcac gtgcgtggtg     840
gtggacgtga gccacgaaga ccccgaggtc cagttcaact ggtacgtgga cggcgtggag     900
gtgcataatg ccaagacaaa gccgcgggag gagcagtaca acagcacgta ccgtgtggtc     960
agcgtcctca ccgtcctgca ccaggactgg ctgaatggca aggagtacaa atgcaaggtc    1020
tccaacaaag ccctcccagc ccccatcgag aaaaccatct ccaaagccaa agggcagccc    1080
cgagaaccac aggtgtacac cctgcccca tcccgggatg agctgaccaa gaaccaggtc     1140
agcctgacct gcctggtcaa aggcttctat cccagcgaca tcgccgtgga gtgggagagc    1200
aatgggcagc cggagaacaa ctacaagacc acgcctcccg tgctggactc cgacggctcc    1260
ttcttccttt acagcaagct caccgtggac aagagcaggt ggcagcaggg gaacgtcttc    1320
tcatgctccg tgatgcatga ggctctgcac aaccactaca cgcagaagag cctctccctg    1380
tctccgggta aatga                                                     1395
```

<210> SEQ ID NO 40
<211> LENGTH: 239
<212> TYPE: PRT
<213> ORGANISM: Artificial
<220> FEATURE:
<223> OTHER INFORMATION: chPcMab-47 light chain.

<400> SEQUENCE: 40

```
Met Asp Phe Gln Val Gln Ile Phe Ser Phe Leu Leu Ile Ser Ala Ser
 1               5                  10                  15

Val Ile Met Ser Arg Gly Gln Ile Val Leu Thr Gln Ser Pro Ala Ile
            20                  25                  30

Met Ser Ala Ser Leu Gly Glu Arg Val Thr Met Tyr Cys Thr Ala Ser
        35                  40                  45

Ser Ser Val Ser Ser Ser Tyr Leu His Trp Tyr Gln Gln Lys Pro Gly
    50                  55                  60

Ser Ser Pro Lys Leu Trp Ile Tyr Gly Thr Ser Asn Leu Ala Ser Gly
65                  70                  75                  80

Val Pro Ala Arg Phe Ser Gly Ser Gly Ser Gly Thr Ser Tyr Ser Leu
                85                  90                  95

Thr Ile Ser Ser Met Glu Ala Glu Asp Ala Ala Thr Tyr Tyr Cys His
            100                 105                 110

Gln Tyr His Arg Pro Pro Leu Thr Phe Gly Ala Gly Thr Lys Leu Glu
        115                 120                 125

Leu Lys Arg Thr Ser Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235
```

<210> SEQ ID NO 41
<211> LENGTH: 720
<212> TYPE: DNA
<213> ORGANISM: Artificial
<220> FEATURE:
<223> OTHER INFORMATION: chPcMab-47 light chain.

<400> SEQUENCE: 41

```
atggatttc  aggtgcagat  tttcagcttc  ctgctaatca  gtgcctcagt  cataatgtcc      60
agaggacaaa  ttgttctcac  ccagtctcca  gcaatcatgt  ctgcatctct  aggggaacgg     120
gtcaccatgt  actgcactgc  cagctcaagt  gtaagttcca  gttacttgca  ctggtaccag     180
cagaagccag  atcctccccc  caaactctgg  atttatggca  catccaacct  ggcttctgga     240
gtcccagctc  gcttcagtgg  cagtgggtct  gggacctctt  actctctcac  aatcagcagc     300
atggaggctg  aagatgctgc  cacttattac  tgccaccaat  atcatcgtcc  cccgctcacg     360
ttcggtgctg  ggaccaagct  ggagctgaaa  cggactagta  ctgtggctgc  accatctgtc     420
ttcatcttcc  cgccatctga  tgagcagttg  aaatctggaa  ctgcctctgt  tgtgtgcctg     480
```

```
ctgaataact tctatcccag agaggccaaa gtacagtgga aggtggataa cgccctccaa    540
tcgggtaact cccaggagag tgtcacagag caggacagca aggacagcac ctacagcctc    600
agcagcaccc tgacgctgag caaagcagac tacgagaaac acaaagtcta cgcctgcgaa    660
gtcacccatc agggcctgag ctcgcccgtc acaaagagct tcaacagggg agagtgttag    720
```

CANCER CELL SPECIFIC ANTI-PODOCALYXIN ANTIBODY AND METHOD FOR PRODUCING SAME

REFERENCE TO A SEQUENCE LISTING SUBMITTED VIA EFS-WEB

The content of the ASCII text file of the sequence listing named "20170809_101611_001US1_seq" which is 45.2 kb in size was created on Feb. 29, 2016 and electronically submitted via EFS-Web on Aug. 9, 2017, is incorporated herein by reference in its entirety.

TECHNICAL FIELD

The present invention relates to a cancer cell-specific anti-podocalyxin antibody, method for producing same, a pharmaceutical composition containing the cancer cell-specific anti-podocalyxin antibody, and the like.

BACKGROUND ART

Podocalyxin is a type I transmembrane protein discovered in renal glomerular epithelial cells (podocytes) (Non-Patent Document 1). Podocalyxin is composed of 558 amino acid residues and has high homology with CD34 which is a hematopoietic stem cell marker.

Podocalyxin has, in an extracellular region thereof, an N-linked glycosylation site, a glycosaminoglycan attachment site, and an O-linked glycosylation site (mucin domain) having a sialic acid rich terminal and is therefore a heavily glycosylated sialomucin. Since glycosylation differs depending on the tissue in which podocalyxin is expressed, it shows various molecular weights. The molecular weight of it sometimes reaches from 150 to 200 kDa. Podocalyxin is involved in cell adhesion, morphogenesis, cancer progression, and the like.

Podocalyxin is negatively charged by glycosylation with a sialic acid, a sulfate group, or the like and inhibits cell adhesion. On the other hand, podocalyxin binds to a cytoskeleton protein or the like and is involved closely in the filtering function of kidneys. It also functions as an adhesion molecule (Non-Patent Document 2). It has been revealed in recent years that in MDCKII cells, a low-molecular-weight G protein Rab and an effector molecule thereof are involved in polarized trafficking of podocalyxin and due to the negative charges generated thereby, podocalyxin takes part in lumen formation (Non-Patent Document 3). It has been reported that podocalyxin is highly expressed in testicular tumor (Non-Patent Document 4), breast cancer (Non-Patent Document 5), prostate cancer (Non-Patent Document 6), ovarian cancer (Non-Patent Document 7), colorectal cancer (Non-Patent Document 8), and pancreatic cancer (Non-Patent Document 9) and it is a marker of malignancy or poor prognosis. Sugar chains on podocalyxin expressed in cancer cells become a ligand for an E-, P-, or L-selectin expressed on epithelial cells and are involved in adhesion, infiltration, or metastasis of cancer cells (Non-Patent Documents 9 and 10).

In addition, podocalyxin is expressed in undifferentiated cells. It has recently been reported that TRA-1-60 or TRA-1-81 which is a marker of undifferentiated cells is an antibody using, as an epitope, keratan sulfate on podocalyxin but reactivity with podocalyxin disappears by induced differentiation of cells (Non-Patent Document 11). BC2L-C which is a lectin purified from Burkholderia cenocepacia is a marker of undifferentiated cells, and it specifically binds to a type O sugar chain on podocalyxin (Non-Patent Document 12). These findings suggest that glycosylation on podocalyxin reflects differentiation of undifferentiated cells, malignancy in cancer cells, or the like.

An antibody which specifically binds only to podocalyxin expressed in cancer cells, if any, is presumed to be useful as a pharmaceutical, a diagnostic agent, a reagent, or the like.

CITATION LIST

Non-Patent Document

Non-Patent Document 1: Kerjaschki D et al., J Clin Invest. 1986; 78(5): 1142-1149.
Non-Patent Document 2: Takeda T et al., J Clin Invest. 2001; 108(2): 289-301.
Non-Patent Document 3: Yasuda K et al., Mol Biol Cell. 2012; 23(16): 3229-3239.
Non-Patent Document 4: Schopperle W M et al., Biochem Biophys Res Commun. 2003; 300(2): 285-290.
Non-Patent Document 5: Somasiri A et al., Cancer Res. 2004; 64(15): 5068-5073.
Non-Patent Document 6: Casey G et al., Hum Mol Genet. 2006; 15(5): 735-741.
Non-Patent Document 7: Cipollone J A et al., Clin Exp Metastasis. 2012; 29(3): 239-252.
Non-Patent Document 8: Larsson A et al., Br J Cancer. 2011; 105(5): 666-672.
Non-Patent Document 9: Dallas M R et al., Am J Physiol Cell Physiol. 2012; 303(6): C616-C624.
Non-Patent Document 10: Thomas S N et al., Am J Physiol Cell Physiol. 2009; 296(3): C505-0513.
Non-Patent Document 11: Schopperle W M et al., Stem Cells. 2007; 25(3): 723-730.
Non-Patent Document 12: Tateno H et al., Stem Cells Transl Med. 2013; 2(4): 265-273.

SUMMARY

Technical Problem

A problem to be overcome by the present invention is to provide a method for producing an antibody against podocalyxin specifically expressed in cancer cells. Another problem to be overcome by the present invention is to provide a cancer cell specific anti-podocalyxin antibody or antigen-binding fragment thereof.

Solution to Problem

The present inventors have thought based on the above-described findings that since the steric structure of podocalyxin is expected to change in cancer cells by glycosylation, it is possible to establish an antibody against podocalyxin expressed specifically in cancer cells by establishing an antibody capable of recognizing podocalyxin having a changed steric structure.

With a view to overcoming the above-described problems, the present inventors caused cancer cell-specific human podocalyxin or a portion thereof to be expressed in cells expressing a cancer cell-specific sugar chain structure and immunized non-human mammals with the cancer cell-specific human podocalyxin or a portion thereof thus expressed. As a result, they have succeeded in establishing an antibody against podocalyxin expressed specifically in cancer cells.

The present invention relates to:

[1] a method for producing an antibody against podocalyxin expressed specifically in cancer cells, including the steps of:

introducing a nucleic acid encoding all or a portion of podocalyxin into cells expressing a cancer cell-specific sugar chain structure and thereby causing cancer cell-specific podocalyxin or a portion thereof to be expressed therein;

immunizing a non-human mammal with the cancer cell-specific podocalyxin or portion thereof to obtain antibodies; and purifying the antibodies by primary screening using a purified cancer cell-specific podocalyxin or a portion thereof;

[2] the method as described above in [1], further including after the primary screening:

a step of comparing reactivity of the antibodies with cancer cells or tissues and reactivity with normal cells or tissues and selecting an antibody having the reactivity with cancer cells or tissues dominantly higher than the reactivity with normal cells or tissues;

[3] the method as described above in [1] or [2], wherein the cells expressing a cancer cell-specific sugar chain structure are cancer cells;

[4] the method as described above in [3], wherein the cancer cells are cells derived from a glioblastoma cell line LN229;

[5] the method as described above in [1] or [2], in which the cells expressing a cancer cell-specific sugar chain structure are cells artificially modified by introducing therein a glycosyltransferase so as to express the cancer cell-specific sugar chain structure;

[6] the method as described above in any of from [2] to [5], in which the step of selecting an antibody which reacts with the cancer cells or tissues and does not react with normal cells or tissues is performed by Immunohistochemistry or Immunocytochemistry;

[7] a cancer cell-specific anti-podocalyxin antibody of any of the following (i) to (iii) or antigen-binding fragment thereof, (i) having at least one of the following six CDRs;

```
heavy chain CDR1:
                                        (SEQ ID NO: 2)
GFNFNTNAMN, heavy chain CDR2:
                                        (SEQ ID NO: 3)
LIRSKSNNYATYYADSVKD, heavy chain CDR3:
                                        (SEQ ID NO: 4)
GYGSY, light chain CDR1:
                                        (SEQ ID NO: 5)
KASQSVNNDVA, light chain CDR2:
                                        (SEQ ID NO: 6)
FASNRYT,
and light chain CDR3:
                                        (SEQ ID NO: 7)
QLDYNSTWT;
```

(ii) having, in the heavy chains CDR 1 to 3 and the light chains CDR 1 to 3 shown in (i), at least one of the heavy chains CDR 1 to 3 and the light chains CDR 1 to 3 including addition, substitution, or deletion of from one to several amino acids; and (iii) having, as at least one of the heavy chains CDR 1 to 3 and the light chains CDR 1 to 3, an amino acid sequence exhibiting 80% or more identity with the amino acid sequence of the heavy chains CDR1 to 3 and the light chains CDR1 to 3 shown in (i), respectively;

[8] a cancer cell-specific anti-podocalyxin antibody or antigen-binding fragment thereof including:

a heavy chain having an amino acid sequence represented by SEQ ID NO: 10;

a heavy chain having, in the amino acid sequence represented by SEQ ID NO: 10, an amino acid sequence including addition, substitution, or deletion of from one to several amino acids; or a heavy chain having an amino acid sequence exhibiting 80% or more identity with the amino acid sequence represented by SEQ ID NO: 10;

[9] a cancer cell-specific anti-podocalyxin antibody or antigen-binding fragment thereof, including:

a light chain having an amino acid sequence represented by SEQ ID NO: 8, a light chain having, in the amino acid sequence represented by SEQ ID NO: 8, an amino acid sequence including addition, substitution, or deletion of from one to several amino acids; or a light chain having an amino acid sequence exhibiting 80% or more identity with the amino acid sequence represented by SEQ ID NO: 8;

[10] the cancer cell-specific anti-podocalyxin antibody or antigen-binding fragment thereof as described above in any of from [7] to [9], which has one or more N-linked sugar chains bound to the Fc region of the antibody and has no fucose bound to N-acetylglucosamine at the reducing end of the N-linked sugar chains;

[11] a nucleic acid encoding any one of the heavy chains CDR1 to 3 and the light chains CDR 1 to 3 as described above in [7];

[12] a nucleic acid encoding any one of the heavy chains as described above in [8] and the light chains as described above in [9];

[13] an expression vector including the nucleic acid as described above in [11] or [12];

[14] a transformant including the expression vector as described above in [13];

[15] a method for producing a cancer-cell specific anti-podocalyxin antibody including the steps of:

expressing an antibody in the transformant as described above in [14], and collecting the antibody;

[16] a pharmaceutical composition having, as an active ingredient, the cancer cell-specific anti-podocalyxin antibody or antigen-binding fragment thereof as described above in any of from [7] to [10];

[17] a pharmaceutical composition having, as an active ingredient, the cancer cell-specific anti-podocalyxin antibody or antigen-binding fragment thereof as described in any of from [7] to [10] to which a substance having an anti-cancer activity has been bound;

[18] the pharmaceutical composition as described above in [16] or [17], which is a preventive or therapeutic agent for cancer;

[19] a cancer testing method, including:

a step of measuring cancer cell-specific podocalyxin in a sample collected from a subject by using a cancer cell-specific anti-podocalyxin antibody or antigen-binding fragment thereof produced by the method described above in any of from [1] to [6] or the cancer cell-specific anti-podocalyxin antibody or antigen-binding fragment thereof described above in any of from [7] to [10]; and

[20] a cancer testing kit, including a cancer cell-specific anti-podocalyxin antibody or antigen-binding fragment thereof produced by the method as described above in any of from [1] to [6] or the cancer cell-specific anti-podocalyxin antibody or antigen-binding fragment thereof as described above in any of from [7] to [10].

Advantageous Effects of Invention

By the method for producing an antibody according to the present invention, an antibody against podocalyxin expressed specifically in cancer cells can be obtained.

By using the antibody against podocalyxin expressed specifically in cancer cells, a pharmaceutical capable of exhibiting an antibody-mediated anti-tumor activity specifically in cancer cells and having reduced side effects can be obtained. It is also useful for the delivery of a drug targeting cancer cells and is highly useful as a diagnostic agent or reagent.

The cancer cell-specific anti-podocalyxin antibody according to the present invention is useful as a reagent for research, a diagnostic agent, or a drug candidate.

BRIEF DESCRIPTION OF DRAWINGS

FIG. 1 shows the flow cytometry results of PcMab-6 which is a cell-specific monoclonal antibody (Cancer-specific mAb: CasMab) against podocalyxin and a cancer-nonspecific anti-podocalyxin antibody PcMab-47 against a breast cancer cell line MCF-7, dermal microvascular endothelial cells, and HEK-293T derived from renal epithelial cells.

FIG. 2 shows the Immunohistochemistry results of PcMab-6 which is CasMab against podocalyxin and an anti-podocalyxin antibody (polyclonal antibody) on a breast cancer tissue array.

FIG. 3 shows the Immunohistochemistry results of PcMab-6 which is CasMab against podocalyxin and PcMab-47 which is an anti-podocalyxin antibody on a breast cancer tissue array.

FIG. 4 shows the flow cytometry results of a mouse-human chimeric antibody chPcMab-6 which is CasMab against podocalyxin and a mouse-human chimeric anti-podocalyxin antibody chPcMab-47 against a glioblastoma cell line LN229, LN229 cells having therein forcibly expressed human podocalyxin (LN229/hPODXL), a malignant mesothelioma cell line MSTO-211H, NCI-H226, a breast cancer cell line MCF-7, an osteosarcoma cell line U2-OS, and a vascular endothelial cell line.

FIG. 5 shows the measurement results of the ADCC activity of chPcMab-6 against LN229/PODXL.

FIG. 6 shows the evaluation of the in vitro activity of chPcMab-6.

FIG. 7 shows the evaluation of the in vivo activity of chPcMab-6 and chPcMab-47.

DESCRIPTION OF EMBODIMENTS

The method for producing an antibody against podocalyxin expressed specifically in cancer cells according to the present invention includes:
a step of introducing a nucleic acid encoding all or a portion of podocalyxin into cells expressing a cancer cell-specific sugar chain structure and thereby causing cancer cell-specific podocalyxin or a portion thereof to be expressed therein;
a step of immunizing a non-human mammal with the cancer cell-specific podocalyxin or portion thereof to obtain antibodies; and
a step of purifying the antibodies by primary screening using a purified cancer cell-specific podocalyxin or a portion thereof.

The term "antibody against podocalyxin expressed specifically in cancer cells" as used herein means an antibody having significant higher reactivity with podocalyxin expressed in cancer cells than reactivity with podocalyxin expressed in normal cells. In one aspect, the "antibody against podocalyxin expressed specifically in cancer cells" reacts with podocalyxin expressed in cancer cells but never reacts with podocalyxin expressed in normal cells. In another aspect, the "antibody against podocalyxin expressed specifically in cancer cells" has markedly high reactivity with podocalyxin expressed in cancer cells, while it reacts to some extent with podocalyxin expressed in normal cells.

The term "cancer cell-specific anti-podocalyxin antibody" as used herein has the same meaning as the "antibody against podocalyxin expressed specifically in cancer cells".

Podocalyxin is highly expressed in testicular tumor, breast cancer, prostate cancer, ovarian cancer, colorectal cancer, pancreatic cancer, and the like and it is also expressed in normal cells.

Human podocalyxin (BC143318, NM_001018111) is a protein represented by SEQ ID NO: 1 and the term "podocalyxin" as used herein encompasses, in addition to it, functional mutants thereof.

In the present specification, the "antibody" has a structure having two heavy chains (H chains) and two light chains (L chains) associated with each other while being stabilized via a pair of disulfide bonds. The heavy chain is composed of a heavy-chain variable region VH, heavy-chain constant regions CH1, CH2 and CH3, and a hinge region positioned between CH1 and CH2. The light chain is composed of a light-chain variable region VL and a light-chain constant region CL. Among these, a variable region fragment (Fv) composed of VH and VL is a region which is directly involved in antigen binding and imparts the antibody with diversity. Further, an antigen-binding region composed of VL, CL, VH and CH1 is called a Fab region, and a region composed of a hinge region, CH2 and CH3 is called an Fc region.

Of the variable regions, a region in direct contact with an antigen shows particularly large variation and is called "complementarity-determining region" (CDR). A region other than CDR and showing relatively smaller variation is called "framework region" (FR). The light chain variable region and the heavy chain variable region each have three CDRs (heavy chains CDR1 to 3 and light chains CDR1 to 3).

The term "cells expressing a cancer cell-specific sugar chain structure" as used herein may mean any cells insofar as they are cells expressing a cancer cell-specific sugar chain structure. For example, they may be cancer cells or cells obtained by introducing a necessary glycosyltransferase into non-cancer cells and thereby artificially modifying them to express a cancer cell-specific sugar chain structure. Examples of the "cells expressing a cancer cell-specific sugar chain structure" include the following cells:

Cells derived from a glioblastoma cell line LN229.

The present inventors have so far confirmed acceleration of keratan sulfate modification depending on the malignancy of cerebral tumor (Kato Y et al., Biochem Biophys Res Commun. 2008; 369(4): 1041-1046.) and discovered, from a cerebral tumor cell line, LN229 cells in which high keratan sulfate modification has occurred (Hayatsu N et al., Biochem Biophys Res Commun. 2008; 368(2): 217-222). They have reported that podocalyxin is highly expressed in astrocytic tumor in correlation with the malignancy (Hayatsu N et al., Biochem Biophys Res Commun. 2008; 374(2): 394-398). Further, they have reported cancer cell-specific addition of sialic acid to a protein expressed by LN229 cells (Kato Y et al., Sci Rep. 2014; 4: 5924).

- Cells obtained by gene introduction of a glycosyltransferase KSGal6ST into glioblastoma cell line LN464 cells (Hayatsu N et al., Biochem Biophys Res Commun. 2008; 368: 217-222). The present inventors have reported in this document that a highly expressed line of keratan sulfate known to be expressed highly in cerebral tumor tissues can be obtained by gene introduction of a glycosyltransferase KSGal6ST into glioblastoma cell line LN464 cells.
- Cells obtained by gene introduction of a glycosyltransferase into cervical cancer cells (HeLa cells) or leukemia cells (Namalwa cells) (Kimura H et al., Biochem Biophys Res Commun. 1997 Aug. 8; 237(1): 131-137). In this document, the present inventors have observed in detail what sugar chain is added by the gene introduction of a glycosyltransferase into cervical cancer cells (HeLa cells) or leukemia cells (Namalwa cells).
- Cells obtained by gene introduction of glycosyltransferase into Namalwa cells (Kaneko M et al., FEBS Lett. 1999; 452(3): 237-242). In this document, the present inventors have observed in detail what sugar chain is added by the gene introduction of a glycosyltransferase into Namalwa cells.
- Cells obtained by introduction of glycosyltransferase into simian kidney cells (COS1 cells) (Kaneko M et al., Blood. 1997; 90(2): 839-849).
- Cells obtained by introduction of glycosyltransferase into hamster ovarian cells (CHO-Lec1 cells) (Kaneko M et al., FEBS Lett. 2003; 554(3): 515-519).

In the present specification, the "step of introducing a nucleic acid encoding all or a portion of podocalyxin into cells expressing a cancer cell-specific sugar chain structure and thereby causing cancer cell-specific podocalyxin or a portion thereof to be expressed therein" can be performed by those skilled in art in a manner known per se in the art. The method for producing an antibody against podocalyxin expressed specifically in cancer cells according to the present invention is characterized by that cancer cell-specific podocalyxin obtained by introducing a nucleic acid encoding all or a portion of podocalyxin into cancer cells and thereby causing forced expression or a portion of the cancer cell-specific podocalyxin is used as an antigen. As the nucleic acid encoding a portion of podocalyxin, a nucleic acid encoding a portion of podocalyxin to which a cancer cell-specific sugar chain has been bound can be used. As the nucleic acid encoding a portion of podocalyxin to which a cancer cell-specific sugar chain has been bound, a nucleic acid encoding the extracellular region of podocalyxin can be used. In the present specification, the nucleic acid may be any nucleic acid insofar as it can express an intended protein. Examples include DNA, RNA, DNA/RNA chimera, and artificial nucleic acids.

In one aspect, all or a portion of podocalyxin is expressed as a secretory type. This can be achieved by introducing a nucleic acid encoding the extracellular region of podocalyxin into cells expressing a cancer cell-specific sugar chain structure. Podocalyxin expressed as a secretory type can be obtained by purifying a culture supernatant of cells expressing a cancer cell-specific sugar chain structure. For example, podocalyxin is expressed with a proper tag and may be purified by making use of the tag.

In the present specification, the "step of immunizing a non-human mammal with the cancer cell-specific podocalyxin or portion thereof to obtain antibodies" can be carried out by administering the cancer cell-specific podocalyxin or portion thereof to a non-human mammal. The purified cancer cell-specific podocalyxin or portion thereof may be used.

Immunization can be performed, for example, by subcutaneously, intradermally, intramuscularly, intravenously, or intraperitoneally injecting the cancer cell-specific podocalyxin or portion thereof if necessary with an adjuvant.

The step of immunizing a non-human mammal may be performed by causing the cancer cell-specific podocalyxin to be expressed not as a secretory type but as a membrane protein and then administering it as the entire cell to a non-human mammal.

The mammal can be immunized in a manner known per se in the art. For example, it can be immunized by intraperitoneally administering from $1\times10^7$ to $1\times10^9$ cells once/10 days at a plurality of times.

In the present specification, the non-human mammal is typically a mouse but not particularly limited thereto. Examples include rats, hamsters, rabbits, cats, dogs, monkeys, goats, sheep, cows, and horses.

The term "primary screening of the antibodies" as used herein means first screening performed during a procedure of identifying an intended antibody from antibody producing cells. It means, for example, screening using a culture supernatant of a hybridoma producing a monoclonal antibody.

The primary screening of the antibodies preferably includes a step of obtaining a monoclonal antibody and a step of identifying a hybridoma producing the monoclonal antibody.

The primary screening of the antibodies in the present invention is generally performed as follows.

First, podocalyxin or a portion thereof is, together with an affinity tag (FLAG tag, His tag, Myc tag, PA tag, or the like), expressed in cells expressing a cancer cell-specific sugar chain structure and purification is performed using the affinity tag. The cancer cell-specific podocalyxin or portion thereof thus purified is immobilized on an ELISA plate. Then, the antibodies obtained from antibody producing cells are added to the plate and wells in which a reaction has occurred are selected. By this method, cancer cell-specific antibodies can be selected in the initial stage of screening.

The purified cancer cell-specific podocalyxin or portion thereof is not particularly limited insofar as it is a purified protein or a portion thereof. It may be a protein purified after forced expression or a purified endogenic protein.

The method for producing an antibody against podocalyxin expressed specifically in cancer cells according to the present invention may include, after the primary screening, a step of comparing reactivity of the antibodies with cancer cells or tissues and reactivity with normal cells or tissues and selecting an antibody having the reactivity with cancer cells or tissues dominantly higher than the reactivity with normal cells or tissues.

Examples of the cancer cells or tissues include cells or tissues in cerebral tumor, prostate cancer, testicular tumor, kidney cancer, thyroid gland cancer, bladder cancer, breast cancer, ovarian cancer, colorectal cancer, pancreatic cancer, malignant mesothelioma, and osteosarcoma. Examples of the normal cells include vascular endothelial cells and renal epithelial cells. Examples of the normal tissues include systemic blood vessels and kidney.

Examples of the cancer cells or tissues may include cells or tissues of 1) adenocarcinoma (lung adenocarcinoma, liver adenocarcinoma, pancreatic adenocarcinoma, lymph adenocarcinoma, uterine adenocarcinoma, seminal vesicle adenocarcinoma, gastric adenocarcinoma, and the like); 2) basal cell carcinoma (skin cancer and the like); 3) squamous cell carcinoma (intraoral cancer, tongue cancer, laryngeal cancer, esophagus cancer, cervical cancer, esophagus cancer, and the like); 4) sarcoma (lymphangiosarcoma, Kaposi's sarcoma, malignant osteosarcoma, and the like); 5) hematopoietic organ tumor (leukemia such as acute/chromic myeloid leukemia, acute promyelocytic leukemia, and acute/chronic lymphocytic leukemia, lymphoma such as Hodgkin lymphoma and non-Hodgkin lymphoma, multiple myeloma, and the like); and 6) renal cell cancer and the like.

The "step of comparing reactivity of the antibodies with cancer cells or tissues and reactivity with normal cells or tissues" as used herein means a step of reacting cancer cells or tissues with the antibodies obtained by the primary screening and detecting the presence or absence of a bond therebetween while reacting normal cells or tissues with the antibodies obtained by the primary screening and detecting the presence or absence of a bond therebetween. This step can be performed by flow cytometry, immunohistochemistry (IHC), immunocytochemistry (ICC), or the like.

A cancer cell-specific antibody can be obtained by comparing between the reactivity of the antibodies with cancer cells or tissues and the reactivity of the antibodies with normal cells or tissues and then selecting an antibody showing significantly higher reactivity with the cancer cells or tissues than with the normal cells or tissues.

The cancer cell-specific antibody thus selected may then be purified further.

The cancer cell-specific anti-podocalyxin antibody of the present invention may be either a monoclonal antibody or a polyclonal antibody. The cancer cell-specific anti-podocalyxin antibody of the present invention may be any isotype of IgG, IgM, IgA, IgD, and IgE. It may be obtained by immunizing a non-human animal such as mouse, rat, hamster, guinea pig, rabbit, or chicken or it may be a recombinant antibody. It may be a chimeric antibody, a humanized antibody, a fully humanized antibody, or the like. The "chimeric antibody" means an antibody obtained by linking fragments of antibodies derived from different species.

The term "humanized antibody" as used herein means an antibody obtained by substituting, by an amino acid sequence characteristic to a non-human-derived antibody, a position of a human antibody corresponding thereto. Examples of it include antibodies having heavy chains CDR1 to 3 and light chains CDR1 to 3 of an antibody prepared by immunizing a mouse and, with respect to all the other regions including four respective framework regions (FR) of the heavy chains and light chains, derived from the human antibody. Such an antibody may also be called "CDR grafted antibody". The term "humanized antibody" may include a mouse-human chimeric antibody.

The term "antigen-binding fragment" of the anti-podocalyxin antibody as used herein means a fragment of the anti-podocalyxin antibody that binds to podocalyxin. Specific examples include, but are not limited to, Fab composed of VL, VH, CL, and CH1 regions; F(ab')2 having two Fabs connected via a disulfide bond in a hinge region; Fv composed of VL and VH; a single-chain antibody scFv having VL and VH connected to each other via an artificial polypeptide linker; and bispecific antibodies such as diabody, scDb, tandem scFv, and leucine zipper type ones.

In one aspect, the cancer cell-specific anti-podocalyxin antibody or antigen-binding fragment thereof according to the present invention has at least one of the following six CDRs. These CDRs are CDR sequences of PcMab-6.

```
heavy chain CDR1:
                                        (SEQ ID NO: 2)
GFNFNTNAMN.

heavy chain CDR2:
                                        (SEQ ID NO: 3)
LIRSKSNNYATYYADSVKD.

heavy chain CDR3:
                                        (SEQ ID NO: 4)
GYGSY.

light chain CDR1:
                                        (SEQ ID NO: 5)
KASQSVNNDVA.

light chain CDR2:
                                        (SEQ ID NO: 6)
FASNRYT.

light chain CDR3:
                                        (SEQ ID NO: 7)
QLDYNSTWT.
```

The cancer cell-specific anti-podocalyxin antibody or antigen-binding fragment thereof according to the present invention may have any of the above-described six CDRs insofar as it produces the advantage of the present invention. It may have two or more, three or more, four or more, five or more or six CDRs. The greater the number, the more preferable.

The cancer cell-specific anti-podocalyxin antibody or antigen-binding fragment thereof according to the present invention may have at least one of a heavy chain CDR1 containing, in the amino acid sequence represented by SEQ ID NO: 2, addition, substitution, or deletion of from one to several amino acids; a heavy chain CDR2 containing, in the amino acid sequence represented by SEQ ID NO: 3, addition, substitution, or deletion of from one to several amino acids; a heavy chain CDR3 containing, in the amino acid sequence represented by SEQ ID NO: 4, addition, substitution, or deletion of from one to several amino acids; a light chain CDR1 containing, in the amino acid sequence represented by SEQ ID NO: 5, addition, substitution, or deletion of from one to several amino acids; a light chain CDR2 containing, in the amino acid sequence represented by SEQ ID NO: 6, addition, substitution, or deletion of from one to several amino acids; and a light chain CDR3 containing, in the amino acid sequence represented by SEQ ID NO: 7, addition, substitution, or deletion of from one to several amino acids.

In the present specification, the term "amino acid" is used in its broadest meaning and it encompasses not only naturally occurring amino acids but also artificial amino acid variants and derivatives of them. The amino acids may be represented by a commonly used single-letter or three-letter code. In the present specification, examples of the amino acid or derivatives thereof include naturally occurring proteinogenic L-amino acids, non-naturally occurring amino acids, and chemically synthesized compounds having properties known in the art as characteristics of an amino acid. Examples of the non-naturally occurring amino acids include, but are not limited to, α,α-disubstituted amino acids (such as α-methylalanine), N-alkyl-α-amino acids, D-amino acids, β-amino acids, and α-hydroxy acids, each having a main chain structure different from that of naturally occurring amino acids; amino acids (such as norleucine and homohistidine) having a side-chain structure different from that of naturally occurring amino acids; amino acids (such as "homo" amino acids, homophenylalanine, and homohistidine) having extra methylene in the side chain thereof; and amino acids (such as cysteic acid) obtained by substituting a carboxylic acid functional group in the side chain by a sulfonic acid group.

When the term "having addition, substitution, or deletion of from one to several amino acids" is used herein, the number of amino acids to be deleted, substituted, or the like is not particularly limited insofar as the resulting polypeptide retains its function as a CDR. The number of amino acids can be set, for example, at 1, 2, 3, 4, 5, 6, 7, 8, 9, or 10, preferably at 1, 2, 3, or 4. The amino acid to be substituted or added may be, as well as a naturally-occurring proteinogenic amino acid, a non-naturally-occurring amino acid or an amino acid analog. The position of deletion, substitution, or addition of the amino acid may be any site of an original CDR sequence insofar as the function as a CDR is retained.

The cancer cell-specific anti-podocalyxin antibody or antigen-binding fragment thereof according to the present invention may have at least one of a heavy chain CDR1 having an amino acid sequence having 80% or more identity with the amino acid sequence represented by SEQ ID NO: 2; a heavy chain CDR2 having an amino acid sequence having 80% or more identity with the amino acid sequence represented by SEQ ID NO: 3; a heavy chain CDR3 having an amino acid sequence having 80% or more identity with the amino acid sequence represented by SEQ ID NO: 4; a light chain CDR1 having an amino acid sequence having 80% or more identity with the amino acid sequence represented by SEQ ID NO: 5; a light chain CDR2 having an amino acid sequence having 80% or more identity with the amino acid sequence represented by SEQ ID NO: 6; and a light chain CDR3 having an amino acid sequence having 80% or more identity with the amino acid sequence represented by SEQ ID NO: 7.

The term "having 80% or more identity" as used herein means that when two polypeptides having an original sequence and a mutated sequence, respectively, are aligned so that their amino acid sequences show the maximum identity, the number of amino acid residues which they have in common is 80% or more of the number of amino acids of the original sequence.

The identity is not limited insofar as it is 80% or more and the function as a CDR can be retained. It can be set, for example, at 85% or more, 90% or more, 91% or more, 92% or more, 93% or more, 94% or more, 95% or more, 96% or more, 97% or more, 98% or more, or 99% or more.

CDRs having an amino acid sequence obtained by adding, substituting, or deleting an amino acid to, by, or from the amino acid sequences of the heavy chains CDR1 to 3 and the light chains CDR1 to 3, or CDRs having 80% or more identity with the amino acid sequences of the heavy chains CDR1 to 3 and the light chains CDR1 to 3 can be prepared using a known method such as site-specific mutagenesis, random mutagenesis, chain shuffling, or CDR walking. It is well known to those skilled in the art that when the above method is used, CDRs with more mature affinity can be obtained by presenting an antibody or antibody fragment having, in the CDR thereof, a variety of mutations on a phage surface by phage display, followed by screening using an antigen (e.g., Wu et al., PNAS. 1998; 95: 6037-6042.; Schier R et al., J. Mol. Bio. 1996; 263: 551-567.; Schier R et al., J. Mol. Biol. 1996; 255: 28-43.; Yang W P et al., J. Mol. Biol. 1995; 254: 392-403).

In another aspect, the cancer cell-specific anti-podocalyxin antibody or antigen-binding fragment thereof according to the present invention includes:

a light chain having an amino acid sequence represented by SEQ ID NO: 8;

a light chain having, in the amino acid sequence represented by SEQ ID NO: 8, an amino acid sequence including addition, substitution, or deletion of from one to several amino acids; or a light chain having an amino acid sequence having 80% or more identity with the amino acid sequence represented by SEQ ID NO: 8.

The amino acid sequence represented by SEQ ID NO: 8 is an amino acid sequence of the light chain of PcMab-6.

In one aspect, the cancer cell-specific anti-podocalyxin antibody or antigen-binding fragment thereof according to the present invention includes:

a heavy chain having an amino acid sequence represented by SEQ ID NO: 10;

a heavy chain having, in the amino acid sequence represented by SEQ ID NO: 10, an amino acid sequence including addition, substitution, or deletion of from one to several amino acids; or a heavy chain having an amino acid sequence having 80% or more identity with the amino acid sequence represented by SEQ ID NO: 10.

The amino acid sequence represented by SEQ ID NO: 10 is an amino acid sequence of the heavy chain of PcMab-6.

When the term "addition, substitution, or deletion of from one to several amino acids in the amino acid sequence of the heavy chain or light chain" is used herein, the number of amino acids to be added, substituted, or deleted can be set at, for example, 1, 2, 3, 4, 5, 6, 7, 8, 9, or 10. Other terms have the same meaning as described above.

The cancer cell-specific anti-podocalyxin antibody according to the present invention may be an antibody having one or more N-linked sugar chains bound to the Fc region thereof and having no fucose bound to N-acetylglucosamine at the reducing end of the N-linked sugar chain.

For example, the Fc region of an IgG antibody has therein two binding sites of an N-linked sugar chain, to which sites a complex-type sugar chain has been bound. The term "N-linked sugar chain" means a sugar chain to be bound to Asn of an Asn-X-Ser/Thr sequence and has a common structure Man3GlcNAc2-Asn. It is classified into a high mannose type, a hybrid type, a complex type, or the like, depending on the kind of the sugar chain bound to two mannoses (Man) at the non-reducing end.

Although fucose may be bound to N-acetylglucosamine (GlcNAc) at the reducing end of the N-linked sugar chain, it is known that an ADCC activity shows a remarkable increase when fucose is not bound thereto compared with when fucose is bound thereto. This is described in, for example, the pamphlet of WO2002/031140.

Since a remarkable improvement in the ADCC activity may lead to a reduction of a dose of an antibody used as a drug, adverse side effects can be alleviated and at the same time, medical expenses can be reduced.

The cancer cell-specific anti-podocalyxin antibody of the present invention may be used after a substance having an anti-cancer activity is bound thereto.

The term "substance having an anti-cancer activity" as used herein means a substance which causes at least one of reduction (retardation or stopping) of a tumor size, inhibition of tumor metastasis, inhibition (retardation or stopping) of tumor growth, and alleviation of one or plural symptoms associated with cancer. Specific examples include, but are not limited to, toxins, anti-cancer agents, and radioisotopes.

Examples of toxins having an anti-cancer activity include *Pseudomonas* exotoxin (PE) or a cytotoxic fragment thereof (for example, PE38), a diphtheria toxin, and ricin A. The toxin having an anti-cancer activity exhibits toxicity only to cells into which the toxin is incorporated together with the anti-podocalyxin antibody, that is, cancer cells in which podocalyxin is expressed so that it has an advantage of specifically producing an advantage without adversely affecting cells around them. In particular, the cancer cell-specific anti-podocalyxin antibody of the present invention is useful because it specifically binds to anti-podocalyxin expressed in tumor cells.

Examples of the anti-cancer agent include low molecular weight compounds such as adriamycin, daunomycin, mitomycin, cisplatin, vincristine, epirubicin, methotrexate, 5-fluorouracil, aclacinomycin, nitrogen mustards, cyclophosphamide, bleomycin, daunorubicin, doxorubicin, vincristine, vinblastine, vindesine, tamoxifen, and dexamethasone, and proteins such as cytokines activating immunocompetent cells (for example, human interleukin 2, human granulocyte-macrophage colony-stimulating factor, human macrophage colony-stimulating factor, and human interleukin 12).

Examples of the radioisotope having an anti-cancer activity include $^{32}P$, $^{14}C$, $^{125}I$, $^{3}H$, $^{131}I$, $^{211}At$, and $^{90}Y$. The radioisotope also exhibits toxicity to cells around cells to which the anti-podocalyxin antibody binds, that is, cells in which podocalyxin is expressed. In general, cancer cells are not uniform and podocalyxin is not expressed in every cancer cell so that radioisotopes are useful for killing podocalyxin-negative cancer cells around them. Further, when a radioisotope is bound, the cancer cell-specific anti-podocalyxin antibody may be a low molecular weight antibody such as Fab or scFv.

The substance having an anti-cancer activity may be directly bound to the cancer cell-specific anti-podocalyxin antibody by a known method. It may be bound to the cancer cell-specific anti-podocalyxin antibody after being enclosed in a carrier such as liposome.

When the substance having an anti-cancer activity is a protein or a polypeptide, by linking a nucleic acid (which will be described later) encoding the cancer cell-specific anti-podocalyxin antibody of the present invention with DNA encoding the substance having an anti-cancer activity and inserting it into an appropriate expression vector, the substance having an anti-cancer activity and the cancer cell-specific anti-podocalyxin antibody may be expressed as a fusion protein.

(Nucleic Acid)

The present invention relates to a nucleic acid encoding the cancer cell-specific anti-podocalyxin antibody of the present invention. The nucleic acid may be either a naturally occurring nucleic acid or an artificial nucleic acid. Examples include, but are not limited to, DNA, RNA, and a DNA/RNA chimera. The base sequence of the nucleic acid encoding the cancer cell-specific anti-podocalyxin antibody can be determined by a method known to those skilled in the art or a method based thereon and can be prepared by a known method or a method based thereon.

Examples of the nucleic acid encoding the cancer cell-specific anti-podocalyxin antibody of the present invention include, but are not limited to, DNA (SEQ ID NO: 11) encoding the heavy chain of PcMab-6 represented by SEQ ID NO: 10 and DNA (SEQ ID NO: 9) encoding the light chain of PcMab-6 represented by SEQ ID NO: 8.

The nucleic acids encoding respective CDRs of PcMab-6 are included in the DNA sequences represented by these SEQ ID NOS.

(Expression Vector)

The present invention also relates to an expression vector containing the nucleic acid encoding the cancer cell-specific anti-podocalyxin antibody of the present invention. The expression vector can be selected as needed according to a host cell to be used. Examples include a plasmid, a retrovirus vector, an adenovirus vector, an adeno-associated virus (AAV) vector, a plant virus vector such as cauliflower mosaic virus vector or tobacco mosaic virus vector, a cosmid, a YAC, and an EBV-derived episome. The nucleic acid encoding the cancer cell-specific anti-podocalyxin antibody of the present invention can be inserted into these expression vectors by a known method (such as a method using a restriction enzyme).

The expression vector of the present invention may further contain a promoter for controlling the expression of an antibody gene, a replication origin, a selection marker gene, or the like. The promoter and the replication origin may be selected as needed, depending on the nature of the host cell and expression vector.

(Transformant)

The present invention relates to a transformant containing the expression vector of the present invention. The transformant can be obtained by transfecting the expression vector of the present invention into appropriate host cells. Examples of the usable host cells include eukaryotic cells such as mammalian cells (CHO cells, COS cells, myeloma cells, HeLa cells, Vero cells, and the like), insect cells, plant cells, and fungus cells (*Saccharomyces, Aspergillus*, and the like), and prokaryotic cells such as *Escherichia coli* (*E. coli*) and *Bacillus subtilis*.

(Production Method of Antibody)

The cancer cell-specific anti-podocalyxin antibody of the present invention can also be produced by the method described below.

A cancer cell-specific anti-podocalyxin monoclonal antibody can be obtained by isolating antibody producing cells from a non-human mammal immunized with the cancer cell-specific podocalyxin or a portion thereof, fusing them with myeloma cells or the like to obtain a hybridoma, and purifying an antibody produced by the hybridoma. A cancer cell-specific anti-podocalyxin polyclonal antibody can be obtained from the serum of an animal immunized with the cancer cell-specific podocalyxin or a fragment thereof.

When the cancer cell-specific anti-podocalyxin antibody of the present invention is produced using genetic recombination, it may be produced, for example, by transforming a proper host with an expression vector containing the nucleic acid of the present invention, culturing the resulting transformant under appropriate conditions to express an antibody, and then isolating and purifying the antibody by a known method.

Examples of the isolating and purifying method include an affinity column using protein A/G/L or the like, another chromatography column, a filter, ultrafiltration, salting-out, and dialysis. These methods may be used in combination as needed.

An antibody that binds to a predetermined epitope sequence can be prepared using a method known to those skilled in the art or a method based thereon. For example, a peptide containing an epitope sequence is fixed to a solid phase carrier and a bond between the peptide and a plurality of antibodies is detected to obtain an antibody that specifically binds to the epitope.

As the "plurality of antibodies", antibodies obtained by immunizing an animal with an antigen protein or a partial peptide thereof may be used or an antibody library or an antibody fragment library constructed by phage display may be used. When a library constructed by phage display is used, it is also possible to fix a peptide containing an epitope sequence to a solid phase carrier, repeat panning, and thereby obtain an antibody that specifically binds to the epitope.

A mouse-human chimeric antibody and a human CDR grafted antibody can be prepared by cloning an antibody gene from mRNA of hybridomas producing an antibody of an animal other than human and linking it to a portion of a human antibody gene by using genetic recombination technology.

For example, for the preparation of a mouse-human chimeric antibody, cDNA is synthesized using reverse transcriptase from mRNA of hybridomas that produce a mouse antibody, the heavy chain variable region (VH) and the light chain variable region (LH) are cloned by PCR, and then the sequence is analyzed. Next, a 5' primer containing a leader sequence is prepared from an antibody base sequence having a high identity and then a portion of the cDNA from the signal sequence to the 3' end of the variable region is cloned by PCR using the 5' primer and the variable region 3' primer. On the other hand, the constant region of the heavy chain and the light chain of human IgG1 is cloned and for the heavy chain and the light chain, the mouse antibody-derived variable region and the human antibody-derived constant region are linked to each other by Overlapping Hanging using PCR and amplified. The DNA thus obtained is inserted into an appropriate expression vector, followed by transformation to obtain a mouse-human chimeric antibody.

For the preparation of a CDR grafted antibody, a human antibody variable region having the highest homology with a mouse antibody variable region to be used is selected and cloned and the base sequence of CDR is modified by site-selective mutagenesis using a mega-primer method. When humanization of an amino acid sequence constituting a framework region disturbs specific binding to an antigen, an amino acid of a portion of the framework may be converted from a human type to a rat type.

A CDR composed of an amino acid sequence having deletion, substitution or addition of from one to several, preferably one or two amino acids in the original sequence or a CDR composed of an amino acid sequence having 80% or more identity to the original sequence may be prepared using a known method such as site-specific mutagenesis, random mutagenesis, chain shuffling, or CDR walking.

It is well known to those skilled in the art that according to these methods, a CDR having more mature affinity can be obtained by displaying an antibody or antibody fragment having a variety of mutations in CDRs on the phage surface by phage display and screening using an antigen (for example, Wu et al., PNAS. 1998; 95: 6037-6042.; Schier R et al., J. Mol. Bio. 1996; 263: 551-567.; Schier R et al., J. Mol. Biol. 1996; 255: 28-43.; Yang W P et al., J. Mol. Biol. 1995; 254: 392-403). The present invention also relates to an antibody containing a CDR matured in such a manner.

As the cells expressing a cancer cell-specific sugar chain structure, a Trichostatin A-treated chicken B cell-derived DT40 cell line may be used and as the method for producing an antibody, an Adlib method for obtaining an antibody producing line from the Trichostatin A-treated chicken B cell-derived DT40 cell line (Seo H et al., Nat. Biotechnol. 2002; 6: 731-736.) may be used. Alternatively, as the non-human mammal, KM mice which are mice obtained by destroying a mouse antibody gene and introducing a human antibody gene may be used and as the method for producing an antibody, a method of immunizing KM mice to prepare a human antibody (Itoh K et al., Jpn. J. Cancer Res. 2001; 92: 1313-1321; Koide A et al., J. Mol. Biol. 1998; 284: 1141-1151).

The antigen-binding fragment of the cancer cell-specific anti-podocalyxin antibody according to the present invention may be expressed by the above-described method using DNA encoding the fragment. Alternatively, a full-length antibody is obtained and then treated with an enzyme such as papain or pepsin to fragment it.

The cancer cell-specific anti-podocalyxin antibody according to the present invention may be different in amino acid sequence, molecular weight, isoelectric point, presence/absence of sugar chains, conformation or the like, depending on the preparation method or purification method. However, the antibody thus obtained is encompassed in the present invention insofar as it has a function equivalent to that of the cancer cell-specific anti-podocalyxin antibody of the present invention. For example, the cancer cell-specific anti-podocalyxin antibody of the present invention expressed in prokaryotic cells such as *E. coli* has a methionine residue at the N terminal of the amino acid sequence of the original antibody. The present invention also relates to such an antibody.

When the cancer cell-specific anti-podocalyxin antibody of the present invention is an antibody having an N-linked sugar chain having no fucose bound to N-acetylglucosamine at the reducing end, such an antibody can be produced by a known method or a method based thereon. Such a method for producing an antibody is described in, for example, the pamphlet of WO2002/031140 or Japanese Patent Application Publication No. 2009-225781.

Specifically, for example, the intended cancer cell-specific anti-podocalyxin antibody can be obtained by transforming cells, whose enzymatic activity involved in the synthesis of GDP-fucose or α-1,6-fucosyltransferase activity has been reduced or deleted, by using an expression vector containing DNA encoding the cancer cell-specific anti-podocalyxin antibody of the present invention, culturing the transformant thus obtained, and then purifying it.

Examples of the enzyme involved in synthesis of GDP-fucose include GDP-mannose 4,6-dehydratase (GMP), GDP-keto-6-deoxymannose 3,5-epimerase, 4-reductase (Fx), and GDP-beta-L-fucose pyrophosphorylase (GFPP).

Here, the cells are not particularly limited, but are preferably mammalian cells. For example, CHO cells having the above-described enzymatic activity reduced or deleted may be used.

Although the antibody composition obtained by the above method may contain an antibody having fucose bound to N-acetylglucosamine at the reducing end, a proportion of the fucose-bound antibody is 20 wt % or less, preferably 10 wt % or less, more preferably 5 wt % or less, most preferably 3 wt % or less, each based on the total weight of the antibodies.

Further, the antibody having an N-linked sugar chain having no fucose bound to N-acetylglucosamine at the reducing end may also be obtained by introducing an expression vector containing DNA encoding the cancer cell-specific anti-podocalyxin antibody of the present invention into insect eggs, hatching and growing the insects, and crossbreeding them if necessary to produce a transgenic insect, and extracting the cancer cell-specific anti-podocalyxin antibody from the transgenic insect or a secretion thereof. As the insect, a silkworm may be used. In this case, the antibody can be extracted from silkworm cocoons.

Although the antibody composition obtained using the above method may also contain an antibody having fucose bound to N-acetylglucosamine at the reducing end, a proportion of the fucose-bound antibody is 20 wt % or less, preferably 10 wt % or less, more preferably 5 wt % or less, most preferably 3 wt % or less, each based on the total weight of the antibodies.

(Activity of Cancer Cell-Specific Anti-Podocalyxin Antibody of the Present Invention)

The drug efficacy mechanism of antibody drugs is based on two biological activities of antibodies. One of them is a target antigen-specific binding activity, which is an activity neutralizing the function of a target antigen molecule through binding thereto. Functional neutralization of the target antigen molecule is exhibited through the Fab region.

The other one is a biological activity of an antibody called "effector activity". The effector activity is exhibited as antibody-dependent cellular cytotoxicity (ADCC), complement-dependent cytotoxicity (CDC), direct induction of apoptosis, or the like through the Fc region of an antibody.

The activities of the cancer cell-specific anti-podocalyxin antibody of the present invention can be measured in the following methods.

(1) Binding Activity

The binding activity of an antibody can be measured by a known method, for example, ELISA (enzyme-linked immunosorbent assay), EIA (enzyme immunoassay), RIA (radioimmunoassay), a fluorescent antibody method, or an FACS method.

(2) ADCC Activity

The term "ADCC activity" means a target cell damaging activity by, when the antibody of the present invention binds to the cell surface antigen of target cells, Fcγ receptor-bearing cells (effector cells) bound to the Fc portion of the antibody through its Fcγ receptor.

The ADCC activity can be known by mixing target cells in which podocalyxin is expressed, effector cells, and the cancer cell-specific anti-podocalyxin antibody of the present invention, and measuring the degree of ADCC. As the effector cells, for example, mouse splenocytes, or monocytes isolated from the human peripheral blood or bone marrow can be used. As the target cells, for example, podocalyxin-positive cancer cells can be used. The activity can be measured by labeling target cells with 51Cr or the like in advance, adding the antibody of the present invention to the resulting cells, incubating the resulting mixture, adding effector cells to the target cells at a ratio adequate therefor, incubating the resulting mixture, collecting the supernatant, and then counting the label in the supernatant.

(3) CDC Activity

The term "CDC activity" means cellular cytotoxicity caused by a complement system.

The CDC activity can be measured by carrying out measurement using, in the ADCC activity test, a complement instead of the effector cells.

(4) Tumor Growth Inhibitory Activity

The tumor growth inhibitory activity can be measured using a tumor model animal. For example, a tumor is subcutaneously implanted into a mouse and the cancer cell-specific anti-podocalyxin antibody of the present invention is administered thereto. A tumor growth inhibitory effect can be measured by comparing the volume of the tumor tissue between a non-administered group and an administered group.

The tumor growth inhibitory activity may result from inhibition of growth of individual cells or may result from induction of apoptosis.

(Pharmaceutical Composition)

The cancer cell specific anti-podocalyxin antibody or antigen-binding fragment thereof according to the present invention may be used for prevention or treatment of a cancer that expresses podocalyxin. A pharmaceutical composition according to one aspect of the present invention contains the cancer cell specific anti-podocalyxin antibody or antigen-binding fragment according to the present invention as an active ingredient and further contains a pharmacologically acceptable carrier or additive.

The cancer cell specific anti-podocalyxin antibody or antigen-binding fragment thereof according to the present invention may be used for delivery of a drug targeting tumor cells. A pharmaceutical composition according to another aspect of the present invention contains the cancer cell specific anti-podocalyxin antibody or antigen-binding fragment thereof to which the above-described substance having an anti-cancer activity or another anti-cancer agent has been bound and it further contains a pharmacologically acceptable carrier or additive.

Examples of the carrier and additive include, but are not limited to, water, saline, phosphate buffer, dextrose, pharmaceutically acceptable organic solvents such as glycerol and ethanol, collagen, polyvinyl alcohol, polyvinylpyrrolidone, carboxy vinyl polymers, carboxymethylcellulose sodium, sodium polyacrylate, sodium alginate, water-soluble dextran, sodium carboxymethyl starch, pectin, methylcellulose, ethylcellulose, xanthan gum, gum arabic, casein, agar, polyethylene glycol, diglycerin, glycerin, propylene glycol, petrolatum, paraffin, stearyl alcohol, stearic acid, human serum albumin, mannitol, sorbitol, lactose, and surfactants.

The pharmaceutical composition of the present invention may be provided in a variety of forms such as a solution (for example, an injection), a dispersion, a suspension, a tablet, a pill, a powder, or a suppository. A preferred aspect is an injection and parenteral (for example, intravenous, transdermal, intraperitoneal, or intramuscular) administration is preferred.

The pharmaceutical composition according to the present invention is effective for the treatment of podocalyxin-related diseases, in particular, cancer.

Examples of the podocalyxin-related cancer include, but not limited to, cerebral tumor, prostate cancer, testicular tumor, kidney cancer, thyroid gland cancer, bladder cancer, breast cancer, ovarian cancer, colorectal cancer, pancreatic cancer, malignant mesothelioma, and osteosarcoma. The cancer cell-specific anti-podocalyxin antibody according to the present invention is particularly useful for these cancers.

The present invention also relates to a method of treating a podocalyxin-related disease, including administering a therapeutically effective amount of the cancer cell-specific anti-podocalyxin antibody or antigen-binding fragment thereof according to the present invention.

The term "therapeutically effective amount" as used herein means an amount of an active substance capable of alleviating one or more symptoms of a disease to be treated to a certain extent. For an anti-cancer agent, it means an amount that causes at least one of reduction of a tumor size, inhibition (retardation or stopping) of tumor metastasis, inhibition (retardation or stopping) of tumor growth, and alleviation of one or more symptoms associated with cancer.

Specifically, the dose of the cancer cell-specific anti-podocalyxin antibody or antigen-binding fragment thereof according to the present invention may be, for example, from 0.025 to 50 mg/kg, preferably from 0.1 to 50 mg/kg, more preferably from 0.1 to 25 mg/kg, still more preferably from 0.1 to 10 mg/kg or from 0.1 to 3 mg/kg, but is not limited thereto.

(Testing Method, Test Drug, Testing Kit)

As described above, podocalyxin is high expressed in specific cancer cells. The cancer cell-specific anti-podocalyxin antibody according to the present invention is therefore useful for the diagnosis of a cancer in which podocalyxin is highly expressed such as cerebral tumor, prostate cancer, testicular tumor, kidney cancer, thyroid gland cancer, bladder cancer, breast cancer, ovarian cancer, colorectal cancer, pancreatic cancer, malignant mesothelioma, or osteosarcoma. The cancer cell-specific anti-podocalyxin antibody according to the present invention specifically binds to cancer cells so that it is particularly useful for the diagnosis.

The present invention also relates to a test drug of cancer containing the cancer cell-specific anti-podocalyxin antibody of the present invention, use of the antibody for testing of cancer, and a testing method of cancer using the cancer cell-specific anti-podocalyxin antibody of the present invention.

When the cancer cell-specific anti-podocalyxin antibody of the present invention is used in the testing method of cancer, for example, the tissue, serum, cerebrospinal fluid, urine, or body fluid (such as saliva or sweat) collected from a subject and suspected to have a cancer can be used as a sample to be tested. Podocalyxin is a membrane protein and is known to be secreted in the serum.

Examples of the testing method include, but are not limited to, immunoassay, aggregation method, turbidimetric method, Western blotting method, and surface plasmon resonance (SPR) method.

Of these, preferred is immunoassay that makes use of an antigen antibody reaction between the cancer cell-specific anti-podocalyxin antibody of the present invention which is detectably labeled and cancer cell-specific podocalyxin in a sample and thereby determines the amount of cancer cell-specific podocalyxin.

Immunoassay uses a detectably labeled cancer cell-specific anti-podocalyxin antibody or an antibody (secondary antibody) against the detectably labeled cancer cell-specific anti-podocalyxin antibody. It is classified, by an antibody labeling method, into enzyme immunoassay (EIA or ELISA), radioimmunoassay (RIA), fluorescence immunoassay (FIA), fluorescence polarization immunoassay (FPIA), chemiluminescence immunoassay (CLIA), and the like and any of them is usable in the method of the present invention.

In ELISA, an antibody labeled with an enzyme such as peroxidase or alkaline phosphatase is used: in RIA, that labeled with a radioactive substance such as $^{125}I$, $^{131}I$, $^{35}S$, or $^{3}H$ is used; in FPIA, that labeled with a fluorescent substance such as fluorescein isothiocyanate, rhodamine, dansyl chloride, phycoerythrin, tetramethylrhodamine isothiocyanate, or near-infrared fluorescent material is used; and in CLIA, that labeled with a luminescent substance such as luciferase, luciferin, or aequorin is used. In addition, an antibody labeled with nanoparticles such as colloidal gold or quantum dot can be detected.

In immunoassay, detection may also be carried out by labeling the cancer cell-specific anti-podocalyxin antibody with biotin and then binding avidin or streptavidin labeled with an enzyme or the like to the antibody.

Among immunoassays, ELISA using enzyme labeling is preferred because an antigen can be measured conveniently and speedily.

ELISA has competitive assay and sandwich assay. In the competitive assay, the cancer cell-specific anti-podocalyxin antibody is immobilized onto a solid phase support such as microplate and then a sample and the enzyme-labeled cancer specific podocalyxin are added to cause an antigen antibody reaction. After washing, the reaction product is reacted with an enzyme substrate to cause color development and an absorbance is measured. The sample containing a larger amount of podocalyxin shows weaker color development, while that containing a smaller amount of podocalyxin shows stronger color development so that the podocalyxin amount can be determined using a calibration curve.

In the sandwich assay, after the cancer cell-specific anti-podocalyxin antibody is fixed onto a solid phase support and a sample is added to cause a reaction therebetween, another enzyme-labeled cancer cell-specific anti-podocalyxin antibody capable of recognizing an epitope is added to cause a reaction therebetween. After washing, reaction with an enzyme substrate, and color development, an absorbance is measured to determine a podocalyxin amount. Alternatively, in the sandwich assay, it is also possible to, after reaction between the cancer cell-specific anti-podocalyxin antibody immobilized onto a solid phase support and cancer-specific podocalyxin in the sample, add a non-labeled antibody (primary antibody), and add an antibody (secondary antibody) against this non-labeled antibody after labeling with an enzyme.

When the enzyme is a peroxidase, 3,3'-diaminobenzidine (DAB), 3,3'5,5'-tetramethylbenzidine (TMB), or o-phenylenediamine (OPD) can be used as the enzyme substrate. When the enzyme is an alkaline phosphatase, p-nitropheny phosphate (NPP) or the like can be used.

In the present specification, the "solid phase support" is not particularly limited insofar as it permits fixing of an antibody thereonto. Examples include microtiter plates, substrates, beads made of glass, a metal, a resin, or the like, nitrocellulose membranes, nylon membranes, and PVDF membranes. The target substance can be fixed onto such a solid phase support in a known manner.

In the above immunoassay, an aggregation method is also preferred as a method capable of conveniently detecting a trace amount of a protein. Examples of the aggregation method include a latex aggregation method performed by binding an antibody to latex particles.

When the cancer cell-specific anti-podocalyxin antibody is bound to latex particles and mixed with a sample, the antibody-bound latex particles aggregate in the presence of cancer specific podocalyxin. The concentration of an antigen can therefore be determined by exposing the sample to a near infrared light and quantitatively determining the resulting aggregated mass by measurement of absorbance (turbidimetry) or measurement of a scattered light (nephelometry).

The term "testing" as used herein means analyzing a sample collected from a subject in order to obtain data necessary for diagnosis. The testing method of the present invention can be performed, for example, by a test company.

In one aspect, the testing method of the present invention includes a step of analyzing whether a cancer specific podocalyxin amount in the sample of a subject is larger than a cancer specific podocalyxin amount of a non-cancer patient. When the cancer specific podocalyxin amount in the sample of a subject is significantly larger than that of the sample of a non-cancer patient, it is judged that the subject suffers a cancer with high possibility.

In one aspect, the testing method of the present invention includes a step of measuring, with the passage of time, a cancer specific podocalyxin amount in the sample of a patient subjected to cancer treatment and analyzing variation in the cancer specific podocalyxin amount. When the podocalyxin amount tends to increase with the passage of time, it is judged that the patient is likely to have a high risk of recurrence or metastasis of a cancer.

The present invention also relates to a diagnostic agent of cancer containing the cancer cell-specific anti-podocalyxin antibody of the present invention, use of the cancer cell-specific anti-podocalyxin antibody of the present invention for the diagnosis of cancer, and a diagnostic method of cancer using the cancer cell-specific anti-podocalyxin antibody of the present invention. The term "diagnosis" as used herein means that persons involved in medical practice such as doctors judge the possibility of a subject suffering from a cancer or the possibility of recurrence and metastasis of a cancer.

[Testing Kit of Cancer]

A testing kit of cancer according to the present invention is a kit for testing a cancer by using the above-described testing method and it includes the cancer cell-specific anti-podocalyxin antibody.

The testing kit according to the present invention includes a reagent, apparatus, and the like necessary for measuring the amount of podocalyxin by immunoassay making use of an antigen antibody reaction between the cancer cell-specific anti-podocalyxin antibody and cancer specific podocalyxin.

In one aspect, a testing kit is for measuring the amount of cancer specific podocalyxin by sandwich assay and it includes a microtiter plate, a cancer cell-specific anti-podocalyxin antibody for capturing, a cancer cell-specific anti-podocalyxin antibody labeled with an alkaline phosphatase or peroxidase; and an alkaline phosphatase substrate (NPP, or the like), and a peroxidase substrate (DAB, TMB, OPD, etc.).

The capturing antibody and the labeled antibody recognize respectively different epitopes.

In such a kit, first, the capturing antibody is fixed onto the microtiter plate. A sample diluted as needed is then added to the microtiter plate, followed by incubation, removal of the sample, and washing. After addition of the labeled antibody and incubation, the substrate is added to cause color development. The amount of cancer specific podocalyxin can then be determined by analyzing the color development by means of a microtiter plate reader or the like.

In another aspect, the testing kit is for measuring the amount of cancer specific podocalyxin by sandwich assay while using a secondary antibody. It includes a microtiter plate, a cancer cell-specific anti-podocalyxin antibody for capturing, a cancer cell-specific anti-podocalyxin antibody serving as a primary antibody, a cancer cell-specific anti-podocalyxin antibody labeled with an alkaline phosphatase or peroxidase, serving as a secondary antibody; and an alkaline phosphatase substrate (NPP, or the like), and a peroxidase substrate (DAB, TMB, OPD, etc.).

The capturing antibody and the primary antibody recognize respectively different epitopes.

In such a kit, first, the capturing antibody is fixed onto the microtiter plate. A sample diluted as needed is then added to the resulting microtiter plate, followed by incubation, removal of the sample, and washing. After addition of the primary antibody, incubation and washing are carried out. Further, the enzyme-labeled secondary antibody is added. After incubation, the substrate is added to cause color development. The amount of cancer specific podocalyxin can then be determined by analyzing the color development by using a microtiter plate reader or the like. Using the secondary antibody can amplify the reaction and enhance the detection sensitivity.

In a further aspect, the testing kit includes a microtiter plate, a cancer cell-specific anti-podocalyxin antibody serving as a primary antibody, a cancer cell-specific anti-podocalyxin antibody labeled with an alkaline phosphatase or peroxidase; and an alkaline phosphatase substrate or a peroxidase substrate.

In such a kit, first, the microtiter plate is coated with a sample diluted to a proper concentration, followed by the addition of the primary antibody. After incubation and washing, the enzyme-labeled secondary antibody is added, followed by incubation and washing. Then, the substrate is added to cause color development.

The amount of cancer specific podocalyxin can be determined by analyzing color development by using a microtiter plate reader or the like.

It is preferred that each testing kit further includes a buffer, an enzymatic reaction stop solution, a microtiter plate reader, and the like necessary for testing.

The labeled antibody is not limited to an enzyme-labeled antibody and it may be an antibody labeled with a radioactive substance (such as $^{25}I$, $^{131}I$, $^{35}S$, or $^{3}H$), a fluorescent substance (such as fluorescein isothiocyanate, rhodamine, dansyl chloride, phycoerythrin, tetramethylrhodamine isothiocyanate, or near-infrared fluorescent material), a luminescent substance (such as luciferase, luciferin, or aequorin), nanoparticles (colloidal gold or quantum dot) or the like. In addition, it is also possible to use a biotinylated antibody as the labeled antibody and add labeled avidin or streptavidin to the kit.

In a still further aspect, the testing kit of the present invention is for determining the amount of cancer-specific podocalyxin by the latex aggregation method. This kit includes latex sensitized with the cancer cell-specific anti-podocalyxin antibody. After a sample is mixed with the cancer cell-specific anti-podocalyxin antibody, the aggregated mass is quantitatively determined by an optical method. The kit preferably includes, in addition, an aggregation reaction plate for visualizing the aggregation reaction.

The testing kit according to the present invention can also be used as a diagnostic kit. In the testing method and diagnostic method of cancer and the testing kit and diagnostic kit of cancer, the cancer cell-specific anti-podocalyxin antibody of the present invention may be replaced by the antigen-binding fragment thereof.

All the disclosed patent documents and non-patent documents to be cited herein are incorporated herein as an entirety by reference.

EXAMPLES

The present invention will hereinafter be described specifically based on embodiments. The present invention is not limited to or by them. Those skilled in the art can change the present invention into various aspects without departing from the gist of the present invention. Such a change is also encompassed within the scope of the present invention.

<Method>

1. Immunization of Mice with Recombinant Protein and Screening

A stable expression line (LN229/sol-hPODXL) of secretory type human podocalyxin was established by introducing, by the lipofection method (product of Life Technologies), the extracellular region (from 26$^{th}$ to 426$^{th}$ amino acids in SEQ ID NO: 1) of human podocalyxin into LN229 cells (purchased from ATCC) of a human cerebral tumor cell line and performing drug selection by the addition of G418 (product of Life Technologies). To the C terminus of the secretory type human podocalyxin was added PA tag (Fujii Y et al., Protein Expr Purif. 2014; 95: 240-247) developed by the present inventors. The LN229/sol-hPODXL thus obtained was mass cultured on a DMEM medium (product of Wako Pure Chemical Industries) containing a 10% fetal bovine serum (FBS; product of Life Technologies) and the supernatant was collected. The supernatant thus collected was filtered through a 0.22 µm-filter (product of Millipore) and the secretory type podocalyxin was purified using a PA tag system. For elution of the secretory type podocalyxin, 0.1 mg/mL of PA tag peptide (hpp4051: peptide having 12 amino acids) was used. The absorbance at OD280 was measured using NanoDrop Lite (product of Thermo Scientific).

Balb/c mice (female, 5 week old; product of CLEA Japan) were immunized with the purified secretory type podocalyxin. Immunization was performed 5 times at intervals of from 7 to 14 days by intraperitoneally administering, at a time, 100 µg of it suspended in 0.5 mL of PBS. Only the first immunization was performed with a mixture with 0.5 mL of ImjectAlum (product of Thermo Scientific) as an adjuvant. Forty eight hours after the final immunization, the spleen was taken out from the immunized mice and spleen cells were extracted. The spleen cells were fused with mouse myeloma P3U1 cells (purchased from ATCC) by using polyethylene glycol 1,500 (product of Sigma Aldrich). The fused product was cultured for 10 days on a 10% FBS/RPMI medium (product of Wako Pure Chemical Industries) containing hypoxanthine aminopterin and thymidine (HAT; product of Life Technologies). The secreted antibody was subjected to primary screening by ELISA.

As the antigen of ELISA, the secretory type human podocalyxin was immobilized. The secretory type human podocalyxin (1 µg/mL) was immobilized onto MaxiSorp (product of Thermo Scientific) and blocking was performed with 1% BSA/PBS. The hybridoma culture supernatant was used as a primary antibody liquid, while anti-mouse IgG-HRP (product of Dako) was used as a secondary antibody liquid. All the antigen antibody reactions were performed at room temperature and the plate was washed with PBS containing 0.05% Tween-20. For detection, 1-Step Ultra TMB-ELISA (product of Thermo Scientific) was used and absorbance at 655 nm was measured using a microplate reader (product of Bio-rad).

2. Flow Cytometry

In secondary screening, reactivity was investigated using the LN229 cells having therein endogenously expressed human podocalyxin and cells obtained by forced expression of human podocalyxin in the LN229 cells. The monoclonal antibody established was evaluated using, in addition to the above-described cells, a glioblastoma cell line LN229 (purchased from ATCC), a breast cancer cell line MCF-7 (purchased from ATCC), an osteosarcoma cell line U2-OS (purchased from ATCC), and a vascular endothelial cell line (purchased from Cambrex). Per reaction, 1×10$^5$ cells were used. The culture supernatant was added to the cells and the primary antibody was reacted at a concentration of 10 µg/mL for one hour on ice. After washing with 0.1% BSA/PBS, an Alexa488-labeled anti-mouse IgG antibody (1/1,000 dilution, product of Life Technologies) was added and a secondary antibody reaction was performed for 30 minutes on ice. After washing with 0.1% BSA/PBS, analysis was performed using Cell Analyzer EC800 (product of Sony). A number of clones including a clone (PcMab-6) reacting with various cancer cell lines but not reacting with the vascular endothelial cells and a clone (PcMab-47) reacting with both were established.

3. Immunohistochemistry

Various paraffin sections were deparaffined in xylene and ethanol solutions. The resulting sections were subjected to antigen activation in an autoclave by using a citrate buffer having pH 6.0 (product of Dako). Endogenous peroxidase was inactivated with 3% $H_2O_2$. After blocking with SuperBlock (product of Thermo Fisher) at room temperature for 10 minutes, the primary antibody was reacted at a concentration of from 5 to 10 µg/mL at room temperature for one hour. After amplification using a LSAB kit (product of Dako), LSAB2 (product of Dako), or Envision+ (product of Dako), color was developed using DAB (product of Dako).

4. Determination of Amino Acid Sequence and Base Sequence of PcMab-6 and PcMab-47 Antibodies From 1×10$^6$ PcMab-6 hybridoma cells and PcMab-47 hybridoma cells, a total RNA was extracted using a QIAGEN RNeasy mini kit. cDNA synthesis was performed with 5 µg of the total RNA using a SuperScript III First-Strand Syntheses kit. The cDNA was used as a template in the following experiment.

For amplification of the H chain, the following primers were used:

```
HindIII-PcMab6HF1atg:
                                    (SEQ ID NO: 12)
gctaagcttAACATGCTGTTGGGGCTGAAG mIgG1terNotI:
                                    (SEQ ID NO: 13)
ggcggccgcTCATTTACCAGGAGAGTGGGA InF.HindIII-Pc47H:
                                    (SEQ ID NO: 14)
CGGTATCGATAAGCTTAACATGGAAAGGCACTGG InF.Pc47HterNotI:
                                    (SEQ ID NO: 15)
TCTAGAGTCGCGGCCGCTCATTTACCAGGAGAGT
```

The PCR reaction was performed using QIAGEN HotStar HiFidelity DNA polymerase. The reaction was made under the following temperature conditions: first at 95° C. for 5 minutes, next 35 cycles of 94° C. for 15 seconds, 50° C. for 1 minute, and 72° C. for 1 minute, and lastly 72° C. for 10 minutes. The amplified PCR product was purified using FastGene Gel/PCR Extraction. The PcMab6 H chain PCR product was treated at 37° C. for one hour with a restriction enzyme HindIII/NotI and then purified again using a FastGene Gel/PCR Extraction kit. The product was subcloned using Ligation High into a pCAG vector treated similarly with the restriction enzyme HindIII/NotI and purified by the same kit and the base sequence was determined using the vector primer. With respect to the PcMab47 H chain PCR product, the PCR product was purified using the FastGene Gel/PCR Extraction kit and subcloned using an InFusion HD cloning kit into the pCAG vector treated with HindIII/NotI and purified by the same kit. The base sequence was determined using the vector primer.

For amplification of the L-chain, the following primers were used.

```
HindIII-PcMab6L.Flatg:
                                        (SEQ ID NO: 16)
gcgaagcttAAGATGAAGTCACAGACCCAG mIgCKterNotI:
                                        (SEQ ID NO: 17)
ggcggccgcCTAACACTCATTCCTGTTGAA InF.HindIII-Pc47L:
                                        (SEQ ID NO: 18)
CGGTATCGATAAGCTTAAAATGGATTTTCAGGTGCA InF.mIgCKterNotI:
                                        (SEQ ID NO: 19)
TCTAGAGTCGCGGCCGCCTAACACTCATTCCTGT
```

The PCR reaction was performed using QIAGEN HotStar HiFidelity DNA polymerase. The reaction was made under the following temperature conditions: first at 95° C. for 5 minutes, next 35 cycles of 94° C. for 15 seconds, 50° C. for 1 minute, and 72° C. for 1 minute, and lastly 72° C. for 10 minutes. The amplified PCR product was purified using FastGene Gel/PCR Extraction.

The PcMab6 L chain PCR product was treated with a restriction enzyme HindIII/NotI at 37° C. for one hour and then purified again using a FastGene Gel/PCR Extraction kit. The product was subcloned using Ligation High into a pCAG vector treated similarly with the restriction enzyme HindIII/NotI and purified by the same kit and the base sequence was determined using the vector primer.

With respect to the PcMab47 L chain PCR product, the PCR product was purified using a FastGene Gel/PCR Extraction kit and subcloned using an InFusion HD cloning kit into a pCAG vector treated with HindIII/NotI and purified by the same kit. The base sequence was determined using the vector primer.

The base sequence of DNA encoding the PcMab-6 H chain was as shown in SEQ ID NO: 11 and the base sequence of DNA encoding the PcMab-6 L chain was as shown in SEQ ID NO: 9. The base sequence of DNA encoding the PcMab-47 H chain was as shown in SEQ ID NO: 23 and the base sequence of DNA encoding the PcMab-47 L chain was as shown in SEQ ID NO: 21.

The amino acid sequence was predicted from the base sequence. The amino acid sequence of the PcMab-6 H chain was as shown in SEQ ID NO: 10 and the amino acid sequence of the PcMab-6 L chain was as shown in SEQ ID NO: 8. The amino acid sequence of the PcMab-47 H chain was as shown in SEQ ID NO: 22 and the amino acid sequence of the PcMab-47 L chain was as shown in SEQ ID NO: 20.

5. Determination of CDR

The site of CDR was specified from the resulting base sequence by using a sequence prediction soft of immunoglobulin provided on the home page (abYsis) of the following URL.

(http://www.bioinf.org.uk/abysis/sequence_input/key_annotation/key_a nnotation.html)

The amino acid sequences of the heavy chains CDR1 to 3 and the light chains CDR1 to 3 of PcMab-6 were specified as shown in SEQ ID NOS: 2 to 7, respectively.

The amino acid sequences of the heavy chains CDR1 to 3 and the light chains CDR1 to 3 of PcMab-47 were specified as shown in SEQ ID NOS: 24 to 29, respectively.

6. Preparation of Mouse-Human Chimeric PcMab-6 Antibody (chPcMab-6) and Mouse-Human Chimeric PcMab-47 Antibody (chPcMab-47)

In order to prepare a mouse-human chimeric PcMab-6 antibody (chPcMab-6) and a mouse-human chimeric PcMab-47 antibody (chPcMab-47), DNAs encoding the respective VH regions of PcMab-6 and PcMab-47 were amplified by PCR and incorporated in pCAG vectors harboring DNA encoding CH1, hinge region, CH2 region, and CH3 region of human IgG1 (pCAG-hIgG1hG2b/PcMab-6HVH, pCAG-hIgG1hG2b/PcMab-47HVH).

The VH region of PcMab-6 was amplified using the following primer with a pCAG/PcMab-6H plasmid as a template.

```
HindIII-PcMab-6VHFlatg:
                                        (SEQ ID NO: 12)
gctaagcttAACATGCTGTTGGGGCTGAAG PcMab6VHR-BamHI:
                                        (SEQ ID NO: 30)
gccggatccTGAGGAGACTGTGAGAGTGGT
```

The VH region of PcMab-47 was amplified using the following primer with a PCAG/PcMab-47H plasmid as a template.

```
InF.HindIII-Pc47H:
                                        (SEQ ID NO: 14)
CGGTATCGATAAGCTTAACATGGAAAGGCACTGG InFr.PcMab47VHR-BamHI:
                                        (SEQ ID NO: 31)
GGCCCTTGGTGGATCCTGCAGAGACAGTGACCA
```

After amplifying DNA encoding the VL region of PcMab-6 by PCR and amplifying DNA encoding the VL region of PcMab-47 by PCR, the PcMab-6 L chain and the PcMab-47 L chain were incorporated in a pCAG vector harboring DNA encoding the CL region of the K chain of human IgG, respectively (pCAG-hIgCK/PcMab-6L, pCAG-hIgCK/PcMab-47L).

DNA encoding the VL region of PcMab-6 was amplified using the following primer, with a pCAG/PcMab-6L plasmid as a template.

```
HindIII-PcMab6L.Flatg:
                                        (SEQ ID NO: 16)
gcgaagcttAAGATGAAGTCACAGACCCAG PcMab6LVL-BamHI:
                                        (SEQ ID NO: 32)
gccggatccCCGTTTGATTTCCAGCTTGGT
```

DNA encoding the VL region of PcMab-47 was amplified using the following primer, with a pCAG/PcMab-47L plasmid as a template.

```
InF.HindIII-Pc47L:
                                        (SEQ ID NO: 18)
CGGTATCGATAAGCTTAAAATGGATTTTCAGGTGCA InF.PcMab47LVL-SpeI:
                                        (SEQ ID NO: 33)
CAGCCACAGTACTAGTCCGTTTCAGCTCCAGCT
``` pCAG-hIgG1hG2b/PcMab-6HVH (G418)/pCAG-hIgCK/PcMab-6LVL (zeocin) (each, 2.5 µg) or pCAG-hIgG1hG2b/PcMab-47HVH (G418)/pCAG-hIgCK/PcMab-47LVL (zeocin) (each, 2.5 µg) were mixed and transfected into 1×10⁵ CHO cells (corresponding to 1 well of a 6-well plate) by the method of Lipofectamin LTX. After 24 hours, selection of transfected cells was started on a medium containing 500 μg/mL of Zeocin and 1 mg/mL of G418. The reactivity of the supernatant of the selected cells with the LN229 cells having therein forcibly expressed podocalyxin (LN229/hPODXL) was confirmed by flow cytometry.

The highly expressed line of the chPcMab-6 antibody was cultured on a serum-free medium (product of Life Technologies) and a culture supernatant was collected. The culture supernatant was passed through a protein G column (product of GE Healthcare) to purify the chPcMab-6 antibody. The chPcMab-6 antibody has a heavy chain having an amino acid sequence represented by SEQ ID NO: 34 and a light chain having an amino acid sequence represented by SEQ ID NO: 36. The base sequence of DNA encoding the heavy chain is shown in SEQ ID NO: 35 and the base sequence of DNA encoding the light chain is shown in SEQ ID NO: 37. The heavy chain has a VH region of the PcMab-6 antibody and CH1, a hinge region, CH2, and CH3 derived from human IgG1. The light chain has a VL region of the PcMab-6 antibody and CL derived from human kappa.

Similarly, the highly expressed line of the chPcMab-47 antibody was cultured on a serum-free medium (product of Life Technologies) and a culture supernatant was collected. The culture supernatant was passed through Protein G column (product of Ge Healthcare) to purify the chPcMab-47 antibody. The chPcMab-47 antibody has a heavy chain having an amino acid sequence represented by SEQ ID NO: 38 and a light chain having an amino acid sequence represented by SEQ ID NO: 40. The base sequence of DNA encoding the heavy chain is shown in SEQ ID NO: 39 and the base sequence of DNA encoding the light chain is shown in SEQ ID NO: 41. The heavy chain has the VH region of the PcMab-47 antibody and CH1, a hinge region, CH2, and CH3 derived from human IgG1. The light chain has a VL region of the PcMab-47 antibody and CL derived from human kappa.

7. Reactivity of chPcMab-6 Antibody Against Podocalyxin

It was confirmed that the chPcMab-6 antibody showed reactivity with podocalyxin. Used were a glioblastoma cell line LN229 (purchased from ATCC) having therein expressed human podocalyxin, cells obtained by forced expression of human podocalyxin in LN229 cells (LN229/hPODXL), malignant mesothelioma cell lines MSTO-211H and NCI-H226, a breast cancer cell line MCF-7 (purchased from ATCC), an osteosarcoma cell line U2-OS (purchased from ATCC), and a vascular endothelial cell line (purchased from Cambrex). For one reaction, 1×10⁵ cells were used. The culture supernatant was added to the cells and the primary antibody was reacted at a concentration of 10 μg/mL for one hour on ice. After washing with 0.1% BSA/PBS, a FITC-labeled anti-human IgG antibody (1/1000 dilution, product of Life Technologies) was added and a secondary antibody reaction was performed for 30 minutes on ice. After washing with 0.1% BSA/PBS, analysis was performed using Cell Analyzer EC800 (product of Sony).

The results are shown in FIG. 4. As shown in this graph, the chPcMab-6 antibody showed good reactivity with any of the cell lines in which podocalyxin is expressed. It did not react with the vascular endothelial cells which were normal cells. As a negative control, only their secondary antibodies were used.

8. Measurement of ADCC Activity of chPcMab-6 Against Podocalyxin Positive Cells (LN229/PODXL)

Human monocytes (Effector cells) were suspended in RPM11640 (Phenol red-free; product of Takara Bio) and the number of cells was adjusted to 1×10⁷ cells/m L. The concentration of LN229/PODXL (Target cells) labeled with Calcein-AM (product of PromoCell) was adjusted to 1×10⁵ cells/mL and the final concentration of chPcMab-6 was added to give a final concentration of 10 μg/mL. As a control, PBS was used. Human monocytes and LN229/PODXL were mixed to give an Effector/Target (E/T) ratio of 100 and seeded in a 96-well plate. To a positive control (complete release), TritonX-100 diluted to 0.1% was added instead of the human monocytes and to a negative control (natural release), a RPM11640 medium was added instead of the human monocytes. After incubation for 4 hours under the conditions of 37° C. and 5% CO₂ and preparative isolation of 100ℓ of the supernatant after the reaction in a black plate for fluorescence measurement, the fluorescence intensity (excitation wavelength: 485 nm, detection wavelength: 535 nm) was measured using a fluorescence plate reader.

The cytotoxicity (%) was calculated using the following equation:

% Specific lysis(Cytotoxicity)=(average *E/T* ratio−average value of negative control)/(average value of positive control−average value of negative control)×100

<Results>

1) Establishment of Anti-Podocalyxin Antibody

Spleen cells extracted from mice immunized with the secretory type podocalyxin and mouse myeloma P3U1 cells were fused using PEG and the fused cells were seeded in five 96-well plates. Primary screening was performed using an ELISA plate on which the secretory type human podocalyxin was immobilized. The absorbance at 655 nm was 0.45 or more in 49 wells among 480 wells and expansion culture in a 24-well plate was performed. Secondary screening was performed with the supernatant of 48 wells in which cell growth was found. In an ELISA plate on which the secretory type human podocalyxin was immobilized, the absorbance at 655 nm was 0.2 or more in 40 wells among 48 wells. Analysis by flow cytometry was performed further by using LN229 cells in which endogenic human podocalyxin was expressed. Among 48 wells, reaction with LN229 cells was positive in 18 wells. Both in ELISA and flow cytometry, reaction was positive in 15 wells among 48 wells and single cloning of them was performed by limiting dilution. Nine single clones were established. Analysis results by the flow cytometry revealed that they showed reactivity with the LN229 cells and the LN229 cells/human podocalyxin stable expression line and the reactivity with the LN229/human podocalyxin was higher than the reactivity with the LN229 in which endogenic podocalyxin was expressed.

2) Flow Cytometry Using Mouse Antibody (FIG. 1)

Among the newly established antibodies, PcMab-6 (IgG1, kappa) showed high reactivity with the glioblastoma cell lines LN229 and LN229/PODXL, malignant mesothelioma cell lines MSTO-211H and NCI-H226, breast cancer cell line MCF-7, and osteosarcoma cell line U2-OS but hardly showed reactivity with the vascular endothelial cell line. On the other hand, it has been found that PcMab-47, another clone, showed reactivity with all of LN229, LN229/PODXL, malignant mesothelioma cell lines MSTO-211H and NCI-H226, MCF-7, U2-OS, and vascular endothelial cell line. These results suggest that PcMab-6 is a cancer-specific antibody (cancer-specific mAb: CasMab).

3) Immunohistochemistry (FIGS. 2 and 3)

Podocalyxin is known to be expressed highly in breast cancer. PcMab-6 and an anti-podocalyxin antibody (polyclonal antibody: product of R&D) were therefore reacted with a breast cancer tissue array (product of US Biomax) at a concentration of 5 µg/mL. As a result, the polyclonal antibody showed high reactivity not only with the cancer cells of the breast cancer tissue but also with the vascular endothelial cells. On the other hand, it has been found that PcMab-6 showed reactivity only with cancer cells and hardly showed reactivity with the vascular endothelial cells. Similarly, a difference in reactivity with breast cancer between PcMab-6 and PcMab-47 was investigated. PcMab-47, when used at a concentration of 5 µg/mL, showed high reactivity not only with the cancer cells of the breast cancer tissue but also with the vascular endothelial cells. On the other hand, PcMab-6 (10 µg/mL) reacted only with cancer cells but hardly showed reactivity with the vascular endothelial cells. It has therefore been confirmed that also in Immunohistochemistry, PcMab-6 is CasMab.

4) Flow Cytometry Using Mouse-Human Chimeric Antibody (FIG. 4)

The mouse-human chimeric antibody chPcMab-6 (IgG1, kappa), similar to PcMab-6, showed high reactivity with the glioblastoma cell line LN229 and LN229/hPODXL, malignant mesothelioma cell lines MSTO-211H and NCI-H226, breast cancer cell line MCF-7, and osteosarcoma cell line U2-OS but hardly showed reactivity with the vascular endothelial cell line. It has been found, on the other hand, that the mouse-human chimeric antibody chPcMab-47 showed reactivity with all of LN229, LN229/PODXL, malignant mesothelioma cell lines MSTO-211H and NCI-H226, MCF-7, U2-OS, and vascular endothelial cell line. These results suggest that similar to PcMab-6, chPcMab-6 is CasMab.

5) ADCC Activity of chPcMab-6

As shown in FIG. 5, chPcMab-6 showed an ADCC activity against LN229/PODXL.

Measurement of ADCC Activity of chPcMab-6 Against Podocalyxin Positive Cells (LN229/PODXL) (NK Cells)

Human NK cells (Effector cells) were suspended in RPMI1640 (Phenol red-free; product of Takara Bio) and the number of cells was adjusted to $1 \times 10^7$ cells/mL. LN229/PODXL (Target cells) labeled with Calcein-AM (product of PromoCell) was adjusted to a concentration of $1 \times 10^5$ cells/mL and chPcMab-6 was added to give a final concentration of 10 µg/mL or 20 µg/m L. As a control, PBS was used. Human monocytes and LN229/PODXL were mixed to give an Effector/Target (E/T) ratio of 100 and the resulting mixture was seeded in a 96-well plate. As a positive control (complete release), the human monocytes were replaced by TritonX-100 diluted to 0.1% and as a negative control (natural release), the human monocytes were replaced by a RPMI1640 medium. After incubation for 4 hours under the conditions of 37° C. and 5% $CO_2$ and preparative isolation of 100l of the supernatant after the reaction in a black plate for fluorescence measurement, the fluorescence intensity (excitation wavelength: 485 nm, detection wavelength: 535 nm) was measured by a fluorescence plate reader.

The cytotoxicity (%) was calculated by the following equation:

% Specific lysis(Cytotoxicity)=(average E/T ratio–average value of negative control)/(average value of positive control–average value of negative control)×100

Preparation of Core Fucose-Deficient Mouse-Human Chimeric PcMab-6 (chPcMab-6f)

A CRISPR/Cas plasmid of a glycosyltransferase (FUT-8) that transfers a core fucose was introduced into CHO-s cells (product of Thermo Scientific) and CHO-s-fut8-knock out cells were established. pCAG-hIgG1hG2b/PcMab-6HVH (G418)/pCAG-hIgCK/PcMab-6LVL (zeocin) (each 2.5 µg) or pCAG-hIgG1hG2b/PcMab-47HVH (G418)/pCAG-hIgCK/PcMab-47LVL (zeocin) (each 2.5 µg) were mixed and transfected into $1 \times 10^5$ CHO-s/fut8-knock out cells (corresponding to 1 well of a 6-well plate) by the method of Lipofectamin LTX. After 24 hours, selection of transfected cells was started on a medium containing 500 µg/mL of Zeocin and 1 mg/mL of G418. The reactivity of the culture supernatant of the selected cells with the LN229 cells having therein forcibly expressed podocalyxin (LN229/hPODXL) was confirmed by flow cytometry.

The chPcMab-6f antibody highly expressed line was cultured on a serum-free medium (product of Thermo Scientific) and a culture supernatant was collected. The culture supernatant was passed through Protein G Sepharose 4 FF (Fast Flow) (product of GE Healthcare) to purify the chPcMab-6f antibody. The chPcMab-6f antibody has a heavy chain having an amino acid sequence represented by SEQ ID NO: 34 and a light chain having an amino acid sequence represented by SEQ ID NO: 36. The base sequence of DNA encoding the heavy chain is shown in SEQ ID NO: 35 and the base sequence of DNA encoding the light chain is shown in SEQ ID NO: 37. The heavy chain has the VH region of the PcMab-6 antibody and CH1, a hinge region, CH2, and CH3 derived from human IgG1. The light chain has the VL region of the PcMab-6 antibody and CL derived from human kappa chain.

Investigation of Anti-Tumor Effect of Anti-Podocalyxin Antibody

The cell line (CHO/hPODXL) obtained by causing human podocalyxin to be expressed highly in CHO cells was subcutaneously transplanted to 18 nude mice. One day, 4 days, 11 days, and 18 days after the tumor transplantation, the chPcMab-6 antibody, chPcMa47 antibody, and human normal IgG were intraperitoneally administered at 100 µg/mouse. Four days after tumor transplantation, $8.25 \times 10^5$/mouse of human NK cells were administered to the periphery of the tumor of all the mice at and 11 days after the tumor transplantation, $9.125 \times 10^5$/mouse of human NK cells were administered to the periphery of the tumor of all the mice. The size of the tumor was measured 4 days, 7 days, 10 days, 14 days, 17 days, 24 days, 28 days, and 30 days after tumor transplantation. Thirty days after the tumor transplantation, all the mice were dissected.

Results

As shown in FIG. 6, chPcMab-6 showed an ADCC activity against LN229/PODXL. Since there is no significant difference in the activity between the concentration of chPcMab-6 at 10 µg/mL and 20 µg/mL, 10 µg/mL is adequate as the concentration. Compared with the investigation using the monocyte shown in FIG. 5, chPcMab-6 shows an enhanced ADCC activity.

SEQUENCE LISTING FREE TEXT

SEQ ID NO: 1 shows the amino acid sequence of human podocalyxin.

SEQ ID NOS: 2 to 4 show the respective amino acid sequences of heavy chains CDR1 to 3 of PcMab-6.

SEQ ID NOS: 5 to 7 show the respective amino acid sequences of light chains CDR1 to 3 of PcMab-6.

SEQ ID NOS: 8 and 9 show the amino acid sequence and DNA sequence of the light chain of PcMab-6, respectively.

SEQ ID NOS: 10 and 11 show the amino acid sequence and DNA sequence of the heavy chain of PcMab-6, respectively.

SEQ ID NO: 12 shows the DNA sequence of primer HindIII-PcMab6HF1atg.

SEQ ID NO: 13 shows the DNA sequence of primer mIgG1terNotI.

SEQ ID NO: 14 shows the DNA sequence of primer InF.HindIII-Pc47H.

SEQ ID NO: 15 shows the DNA sequence of primer InF.Pc47HterNotI.

SEQ ID NO: 16 shows the DNA sequence of primer HindIII-PcMab6L.F1atg,

SEQ ID NO: 17 shows the DNA sequence of primer mIgCKterNotI.

SEQ ID NO: 18 shows the DNA sequence of primer InF.HindIII-Pc47L.

SEQ ID NO: 19 shows the DNA sequence of primer InF.mIgCKterNotI.

SEQ ID NOS: 20 and 21 show the amino acid sequence and DNA sequence of the light chain of PcMab-47, respectively.

SEQ IS NOS: 22 and 23 show the amino acid sequence and DNA sequence of the heavy chain of PcMab-47, respectively.

SEQ ID NO: 24 to 26 show the respective amino acid sequences of the heavy chains CDR1 to 3 of PcMab-47.

SEQ ID NO: 27 to 29 show the respective amino acid sequences of the light chains CDR1 to 3 of PcMab-47.

SEQ ID NO: 30 shows the DNA sequence of primer PcMab6VHR-BamHI.

SEQ ID NO: 31 shows the DNA sequence of primer InFr.PcMab47VHR-BamHI.

SEQ ID NO: 32 shows the DNA sequence of primer PcMab6LVL-BamHI.

SEQ ID NO: 33 shows the DNA sequence of primer InF.PcMab47LVL-SpeI.

SEQ ID NOS: 34 and 35 show the amino acid sequence and DNA sequence of the heavy chain of chPcmab-6.

SEQ ID NOS: 36 and 37 show the amino acid sequence and DNA sequence of the light chain of chPcmab-6.

SEQ ID NOS: 38 and 39 show the amino acid sequence and DNA sequence of the heavy chain of chPcmab-47, respectively.

SEQ ID NOS: 40 and 41 show the amino acid sequence and DNA sequence of the light chain of chPcmab-47, respectively.

What is claimed is:

1. A cancer cell-specific anti-podocalyxin antibody or antigen-binding fragment thereof, comprising
   (i) a first amino acid sequence comprising the following CDRs:

heavy chain CDR1:
   (SEQ ID NO: 2)
   GFNFNTNAMN, heavy chain CDR2:
   (SEQ ID NO: 3)
   LIRSKSNNYATYYADSVKD,
   and heavy chain CDR3:
   (SEQ ID NO: 4)
   GYGSY;

and
   (ii) a second amino acid sequence comprising the following CDRs:

light chain CDR1:
   (SEQ ID NO: 5)
   KASQSVNNDVA, light chain CDR2:
   (SEQ ID NO: 6)
   FASNRYT,
   and light chain CDR3:
   (SEQ ID NO: 7)
   QLDYNSTWT.

2. The cancer cell-specific anti-podocalyxin antibody or antigen-binding fragment thereof according to claim 1, wherein the first amino acid sequence comprises SEQ ID NO: 10, the second amino acid sequence comprises SEQ ID NO: 8, or both.

3. The cancer cell-specific anti-podocalyxin antibody or antigen-binding fragment thereof according to claim 1, which has one or more N-linked sugar chains bound to a Fc region of the antibody and has no fucose bound to N-acetylglucosamine at a reducing end of the N-linked sugar chains.

4. A nucleic acid encoding the first amino acid sequence and/or the second amino acid sequence as claimed in claim 1.

5. An expression vector comprising the nucleic acid as claimed in claim 4.

6. A transformant comprising the expression vector as claimed in claim 5.

7. A method for producing a cancer-cell specific antipodocalyxin antibody comprising the steps of:
   expressing an antibody in the transformant as claimed in claim 6; and
   collecting the antibody.

8. A pharmaceutical composition, comprising, as an active ingredient, the cancer cell-specific anti-podocalyxin antibody or antigen-binding fragment thereof as claimed in claim 1.

9. A pharmaceutical composition, comprising, as an active ingredient, the cancer cell-specific anti-podocalyxin antibody or antigen-binding fragment thereof as claimed in claim 1 to which a substance having an anti-cancer activity has been bound.

10. The pharmaceutical composition according to claim 8, which is a preventive or therapeutic agent for cancer.

11. A cancer testing method, comprising:
    a step of measuring cancer cell-specific podocalyxin in a sample collected from a subject by using a cancer cell-specific anti-podocalyxin antibody or antigen-binding fragment thereof as claimed in claim 1 to measure the cancer cell-specific podocalyxin.

12. A cancer testing kit, comprising a cancer cell-specific anti-podocalyxin antibody or antigen-binding fragment thereof as claimed in claim 1.

13. A cancer cell-specific anti-podocalyxin antibody or antigen-binding fragment thereof, comprising
    (i) a first amino acid sequence comprising the following CDRs:

heavy chain CDR1:
    (SEQ ID NO: 2)
    GFNFNTNAMN, heavy chain CDR2:
    (SEQ ID NO: 3)
    LIRSKSNNYATYYADSVKD,
    and heavy chain CDR3:
    (SEQ ID NO: 4)
    GYGSY;

and
    (ii) a second amino acid sequence comprising the following CDRs:

light chain CDR1:
    (SEQ ID NO: 5)
    KASQSVNNDVA, light chain CDR2:
    (SEQ ID NO: 6)
    FASNRYT,
    and light chain CDR3:
    (SEQ ID NO: 7)
    QLDYNSTWT;

wherein one or more of the CDRs have one amino acid addition, substitution, or deletion.

14. The cancer cell-specific anti-podocalyxin antibody or antigen-binding fragment thereof according to claim 13, which has one or more N-linked sugar chains bound to a Fc region of the antibody and has no fucose bound to N-acetylglucosamine at a reducing end of the N-linked sugar chains.

15. A nucleic acid encoding the first amino acid sequence and/or the second amino acid sequence as claimed in claim 14.

16. An expression vector comprising the nucleic acid as claimed in claim 15.

17. A transformant comprising the expression vector as claimed in claim 16.

18. A method for producing a cancer-cell specific anti-podocalyxin antibody comprising the steps of:
   expressing an antibody in the transformant as claimed in claim 17; and
   collecting the antibody.

19. A pharmaceutical composition, comprising, as an active ingredient, the cancer cell-specific anti-podocalyxin antibody or antigen-binding fragment thereof as claimed in claim 13.

20. A pharmaceutical composition, comprising, as an active ingredient, the cancer cell-specific anti-podocalyxin antibody or antigen-binding fragment thereof as claimed in claim 13 to which a substance having an anti-cancer activity has been bound.

21. The pharmaceutical composition according to claim 19, which is a preventive or therapeutic agent for cancer.

22. A cancer testing method, comprising:
   a step of measuring cancer cell-specific podocalyxin in a sample collected from a subject by using a cancer cell-specific anti-podocalyxin antibody or antigen-binding fragment thereof as claimed in claim 13 to measure the cancer cell-specific podocalyxin.

23. A cancer testing kit, comprising a cancer cell-specific anti-podocalyxin antibody or antigen-binding fragment thereof as claimed in claim 13.

* * * * *

UNITED STATES PATENT AND TRADEMARK OFFICE
CERTIFICATE OF CORRECTION

PATENT NO. : 10,906,972 B2
APPLICATION NO. : 15/549923
DATED : February 2, 2021
INVENTOR(S) : Kato et al.

It is certified that error appears in the above-identified patent and that said Letters Patent is hereby corrected as shown below:

On the Title Page

Item [56], Page 2, last 3 lines of Column 1, change
"OGASAWARA, ET AL., Development of Cancer-Specific Antibody (CasMab) against Podoplanin, 87th Annual Meeting, October 18, 2014, Page(s) 4T13a-14 (4P-031), Volume 87, Publisher: The Japanese Biochemical Society." to
--OGASAWARA, ET AL., Podoplanin ni Taisuru Gan Tokuiteki Kotai (CasMab) no Kaihatsu, Development of Cancer-Specific Antibody (CasMab) against Podoplanin, 87th Annual Meeting, October 18, 2014, Page(s) 4T13a-14 (4P-031), Volume 87, Publisher: The Japanese Biochemical Society.--

In the Specification

Column 28, Line 5, change "m L" to --mL--

Column 28, Line 18, change "1004" to --100 µL--

Column 29, Line 5, change "m L" to --mL--

Signed and Sealed this
Thirty-first Day of August, 2021

Drew Hirshfeld
*Performing the Functions and Duties of the*
*Under Secretary of Commerce for Intellectual Property and*
*Director of the United States Patent and Trademark Office*